(12) United States Patent
Tong et al.

(10) Patent No.: US 8,216,782 B2
(45) Date of Patent: Jul. 10, 2012

(54) PTTG1 AS A BIOMARKER FOR CANCER TREATMENT

(75) Inventors: Yunguang Tong, Los Angeles, CA (US); Shlomo Melmed, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 12/867,042

(22) PCT Filed: Mar. 13, 2009

(86) PCT No.: PCT/US2009/037178
§ 371 (c)(1),
(2), (4) Date: Aug. 10, 2010

(87) PCT Pub. No.: WO2009/114817
PCT Pub. Date: Sep. 17, 2009

(65) Prior Publication Data
US 2011/0009473 A1 Jan. 13, 2011

Related U.S. Application Data

(60) Provisional application No. 61/036,524, filed on Mar. 14, 2008, provisional application No. 61/147,435, filed on Jan. 26, 2009.

(51) Int. Cl.
*C12Q 1/68* (2006.01)
*A61K 35/12* (2006.01)
*G01N 33/48* (2006.01)

(52) U.S. Cl. .............................. 435/6; 424/277.1; 436/94

(58) Field of Classification Search .................. None
See application file for complete search history.

(56) References Cited

OTHER PUBLICATIONS

PCT International Preliminary Report on Patentability, Issued Sep. 14, 2010 for International Application No. PCT/US09/037178, 6 pages.
Supplementary European Search Report and Written Opinion, issued Nov. 2, 2011, European Application No. EP 09719266.0, 8 pages.
El-Naggar, S.M., et al., Small interfering RNA against PTTG: A novel therapy for ovarian cancer, International Journal of Oncology, Jul. 2007, 31:1, pp. 137-143.
Fujii, T., et al, Overexpression of pituitary tumor transforming gene 1 in HCC is associated with angiogenesis and poor prognosis, Hepatology, Jan. 2006, 43:6, pp. 1267-1275.
Ghayad, S.E., et al, Identification of TACC1, NOV, and PTTG1 as new candidate genes associated iwth endocrine therapy resistance in breast cancer, Journal of Molecular Endocrinology, Nov. 2, 2008, 42:2, pp. 87-103.
Jung, C-R., et al., Adenovirus-mediated transfer of siRNA against PTTG1 inhibits liver cancer cell growth in Vitro and in Vivo, Hepatology, May 1, 2006, 43:5, pp. 1042-1052.
Saez, C., et al., Prognostic significance of human pituitary tumor-transforming gene immunohistochemical expression in differentiated thyroid cancer, Journal of Clinical Endocrinology & Metabolism, Jan. 10, 2006, 91:4, pp. 1404-1409.
Solbach, C., et al., Pituitary tumor-transforming gene expression is a prognostic marker for tumor recurrence in squamous cell carcinoma of the head and neck, BMC Cancer, Oct. 9, 2006, 6:242, pp. 1-8.
Tong, Y., et al., PTTG1 attenuates drug-induced cellular senescence, PLOS One, Aug. 17, 2011, 6:8, pp. 1-13.

*Primary Examiner* — Amy Bowman
(74) *Attorney, Agent, or Firm* — Sean D. Senn; Nixon Peabody LLP

(57) ABSTRACT

The present invention relates to the use of pituitary tumor transforming gene 1 (PTTG1) as a biomarker for diagnosing cancer as well as for determining cancer treatment responsiveness. In one embodiment, the present invention provides a method of treating cancer by inhibiting the expression of PTTG1, and administering a therapeutically effective amount of Aurora kinase inhibitor, HDAC inhibitor and/or ROS-generating agent.

7 Claims, 14 Drawing Sheets

Figure 2
(A)
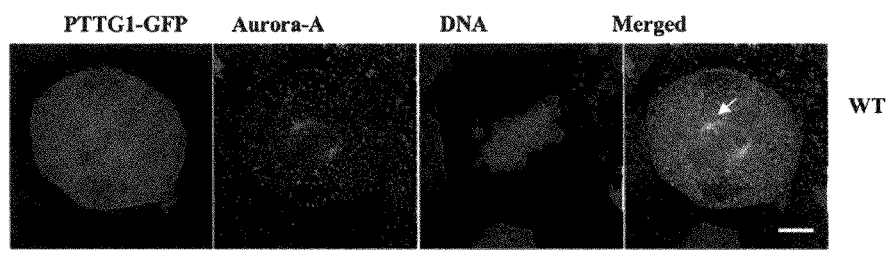
WT
(B)
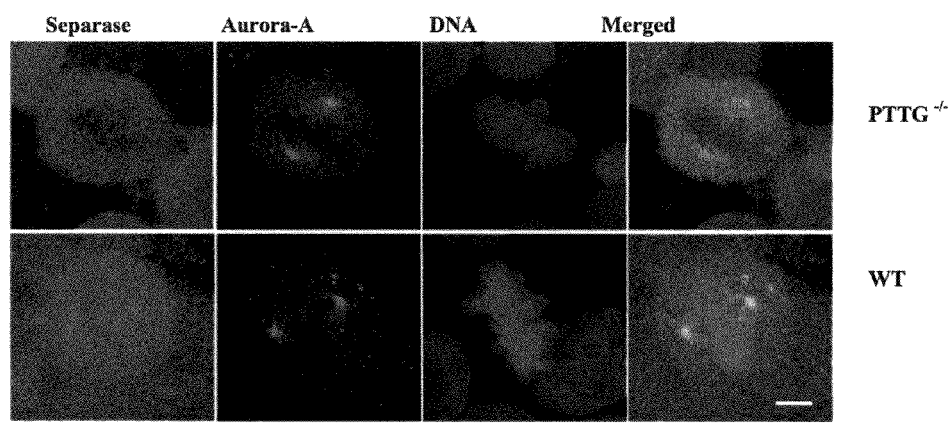
PTTG⁻/⁻
WT
(C)
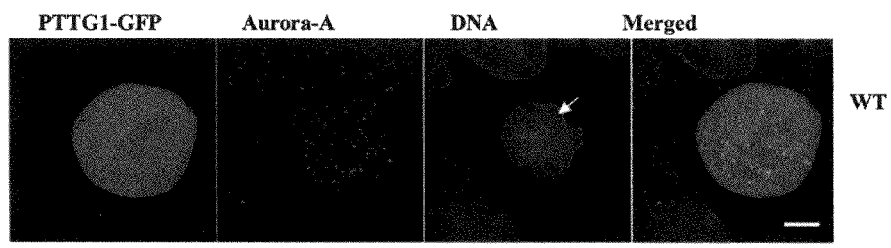
WT

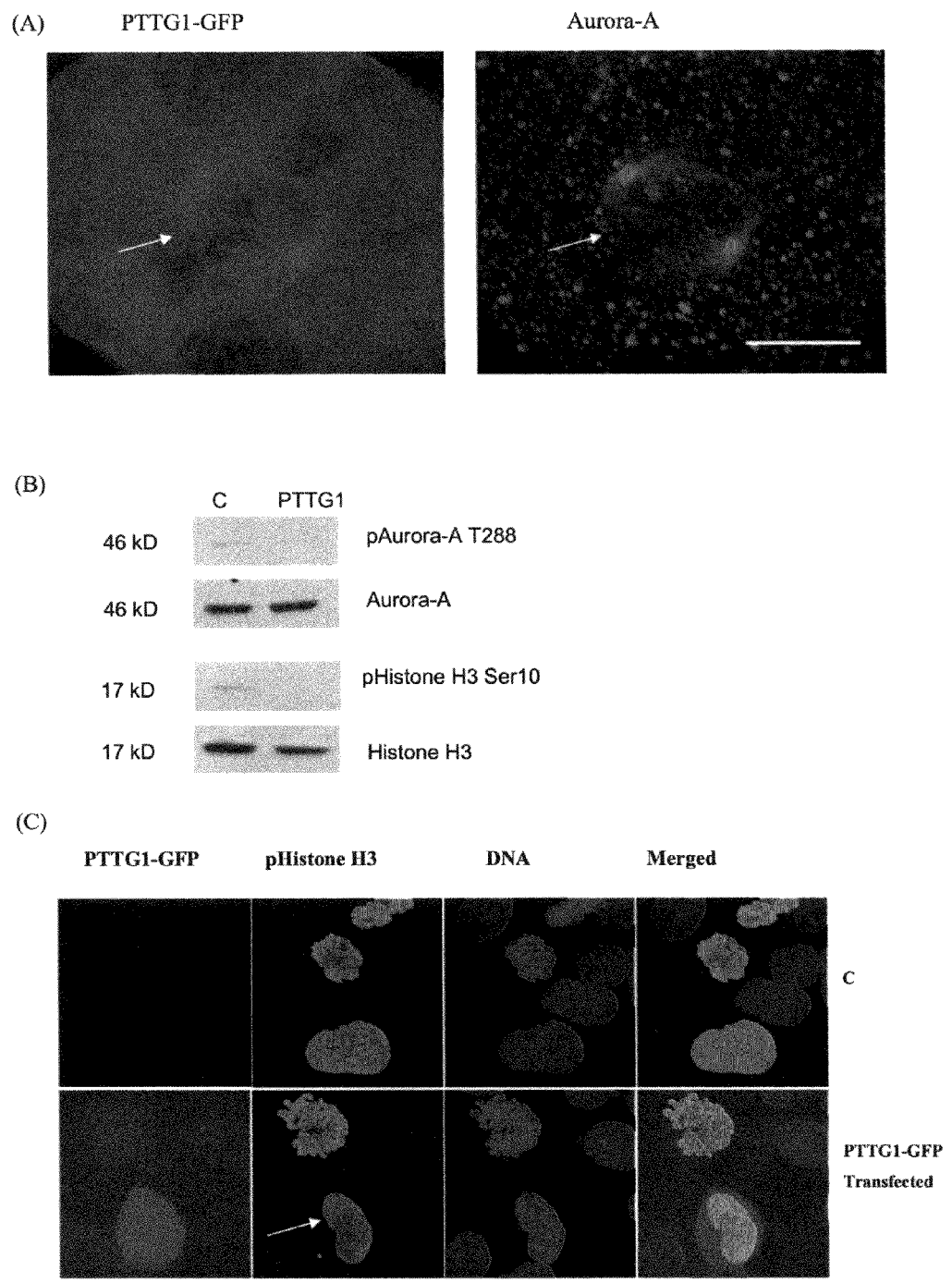

Figure 3
(D)
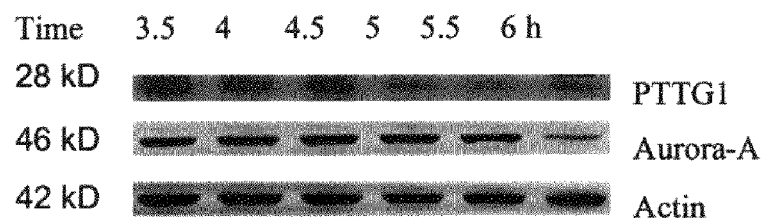
(E)
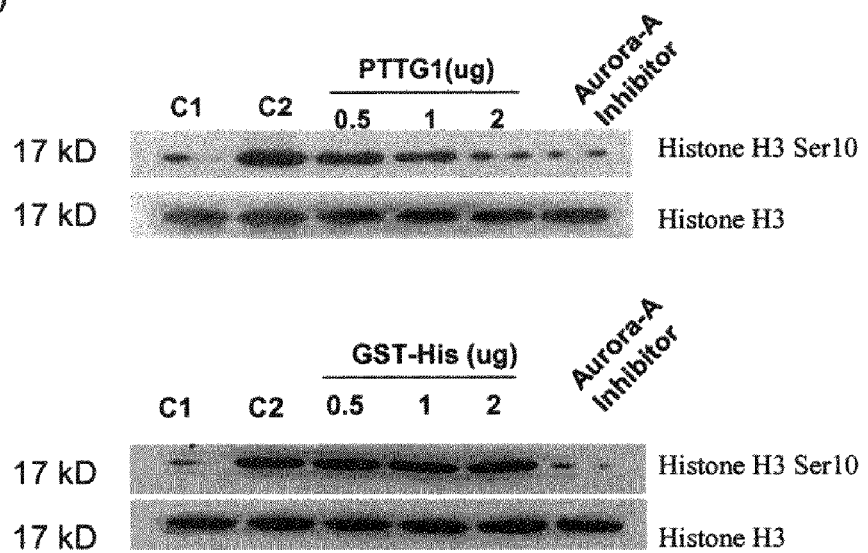

Figure 4
(A)
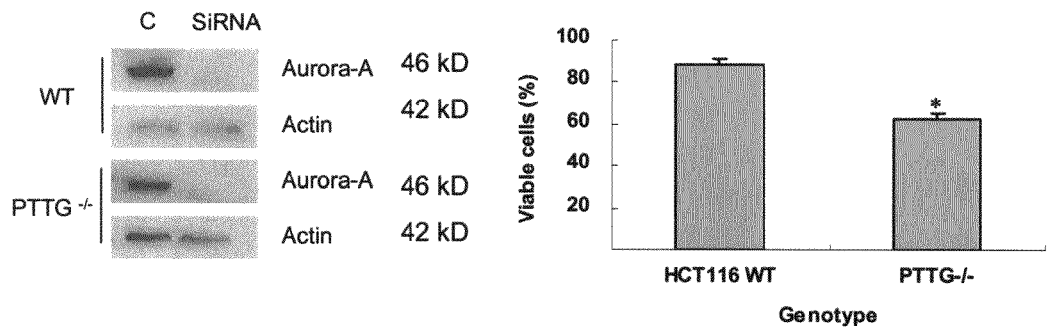
(B)
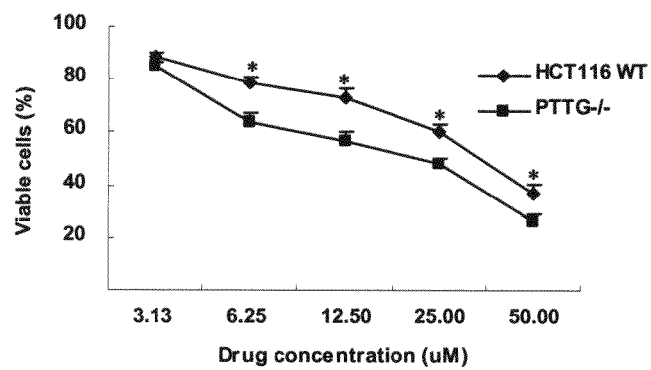
(C)
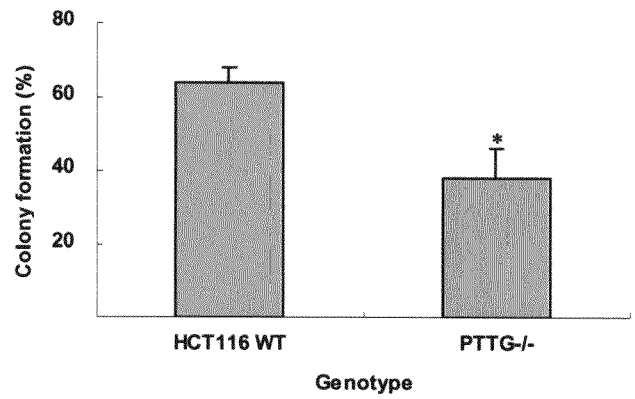

(D)

Figure 5
(A)
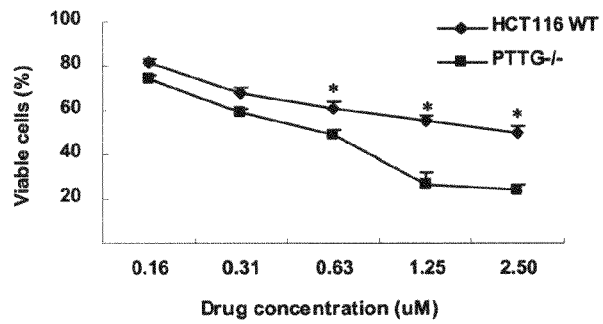
(B)
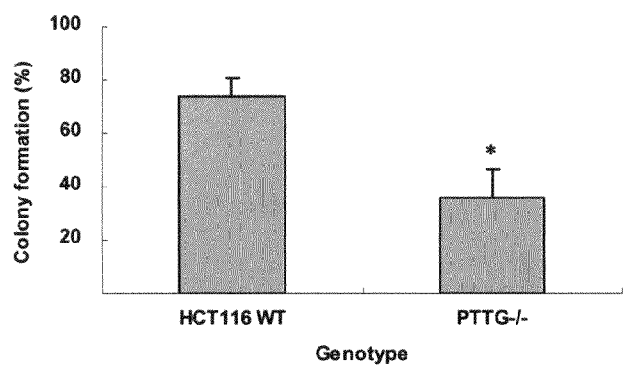
(C)
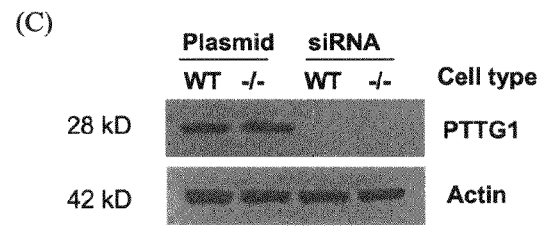
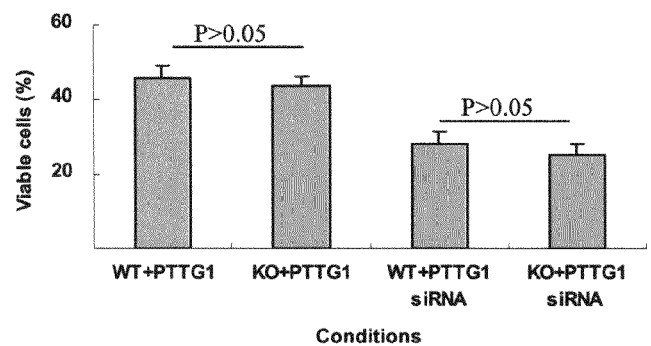

Figure 5
(D)
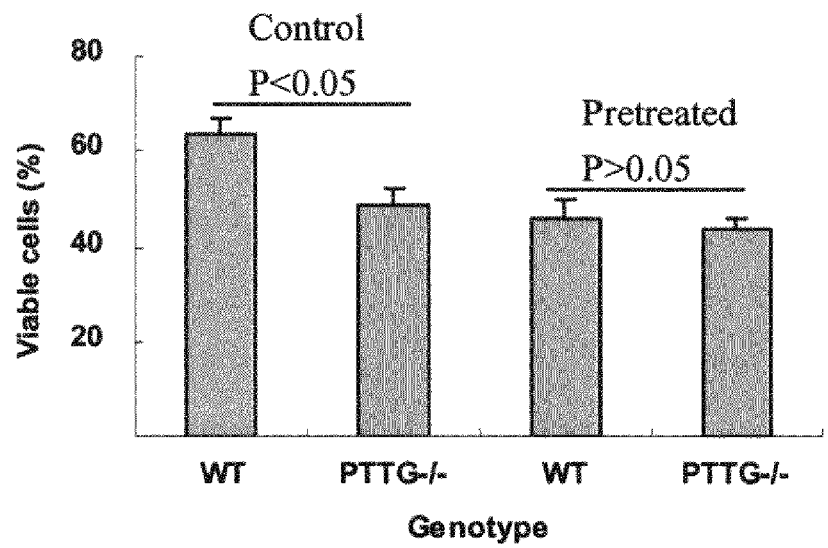
(E)
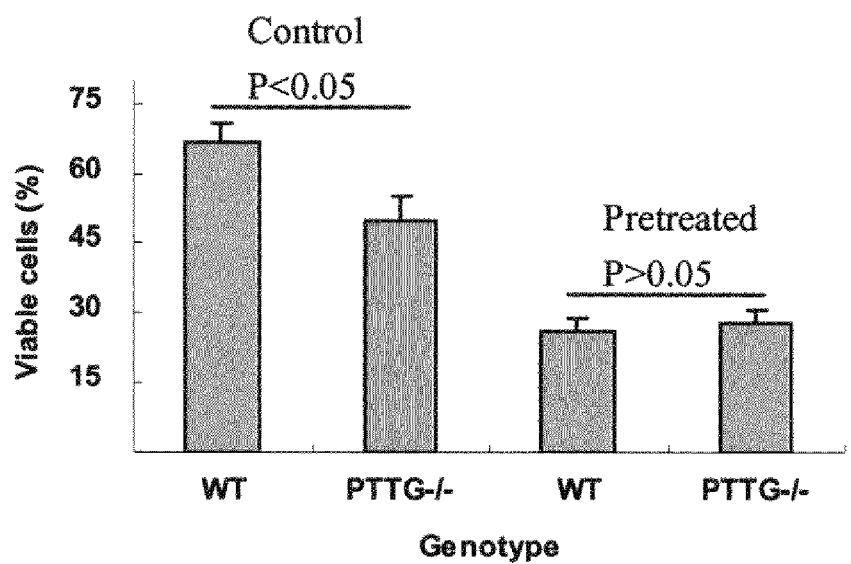

Figure 7
(A)
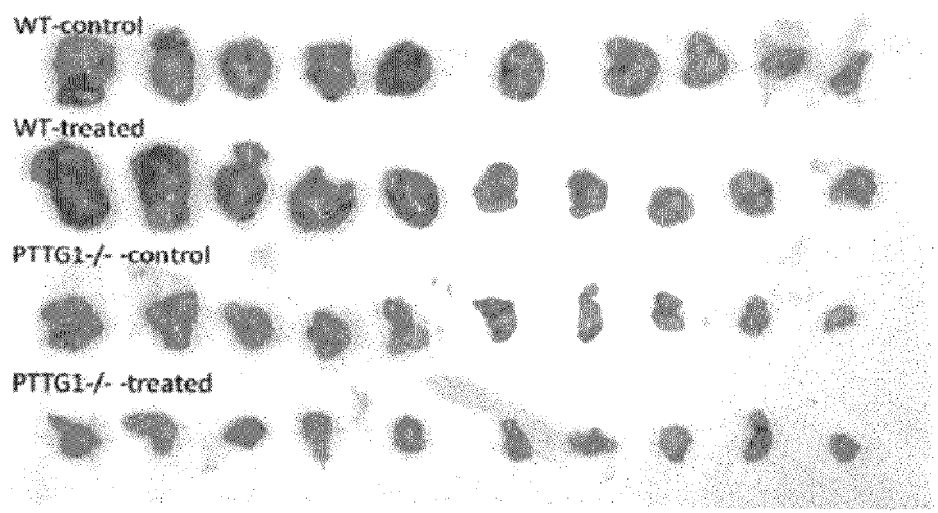
(B)
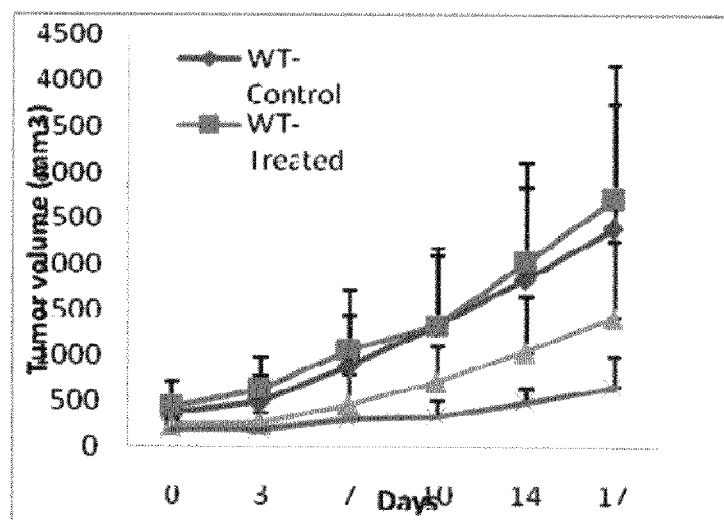

Figure 8
(A)
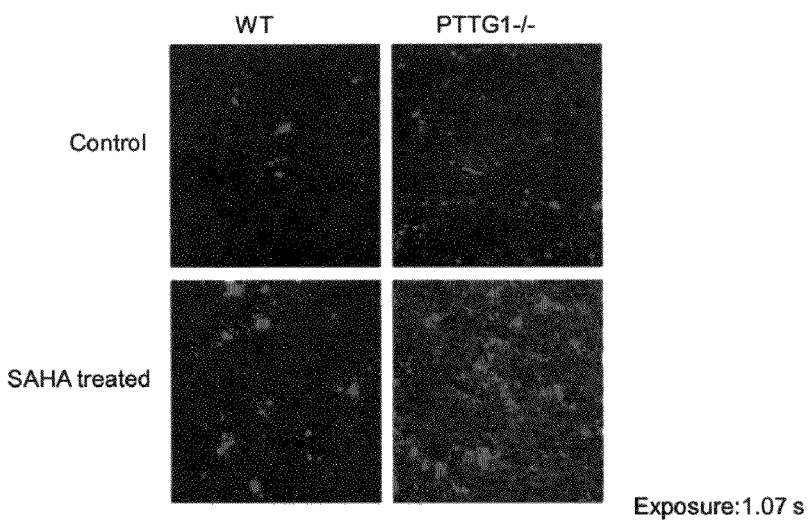
(B)
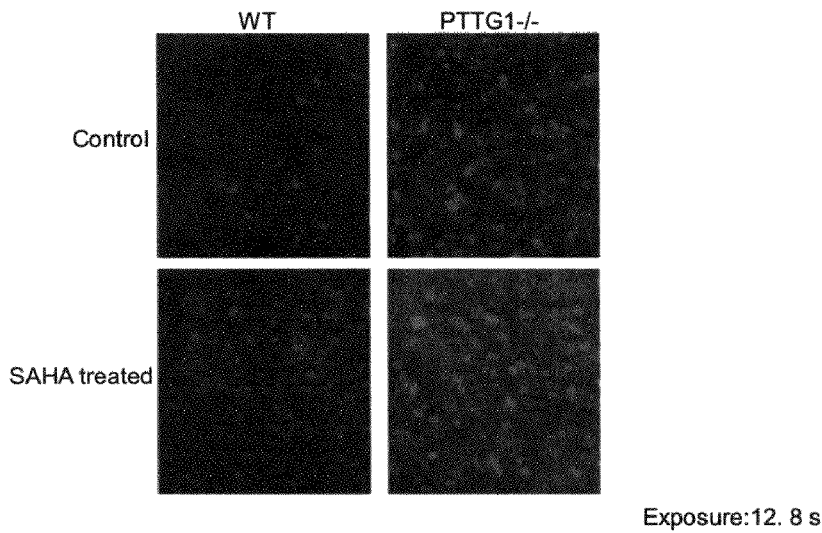

Figure 10
(A)
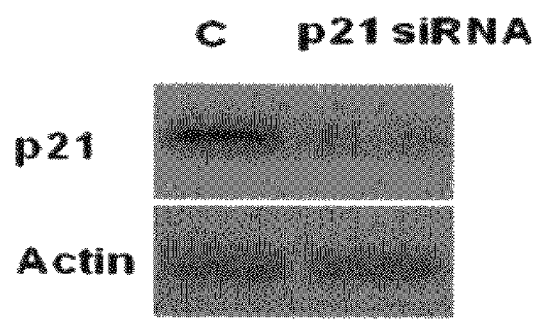
(B)
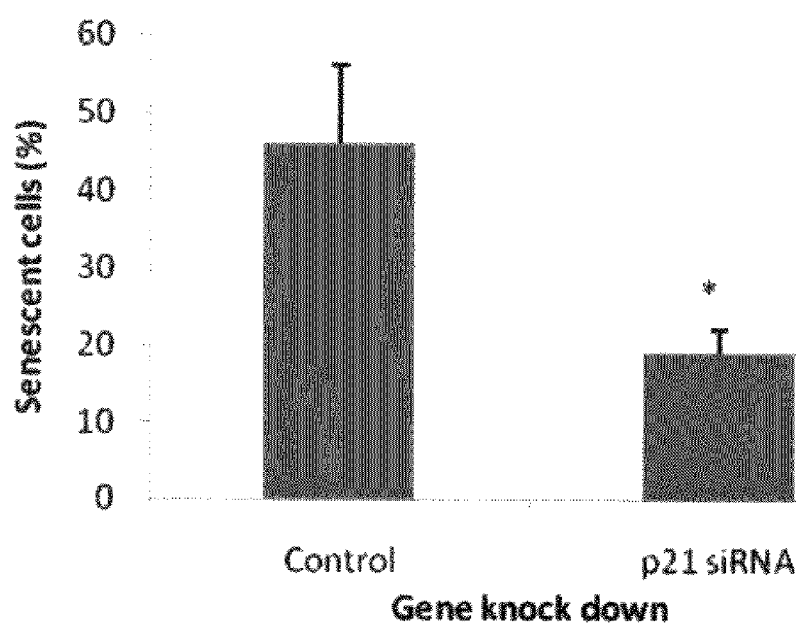

Figure 11
(A)
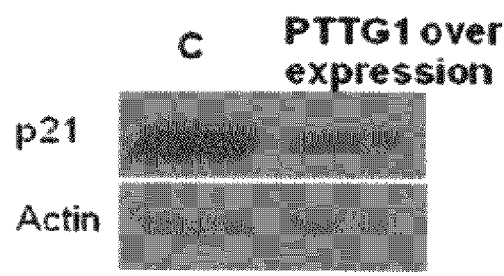
(B)
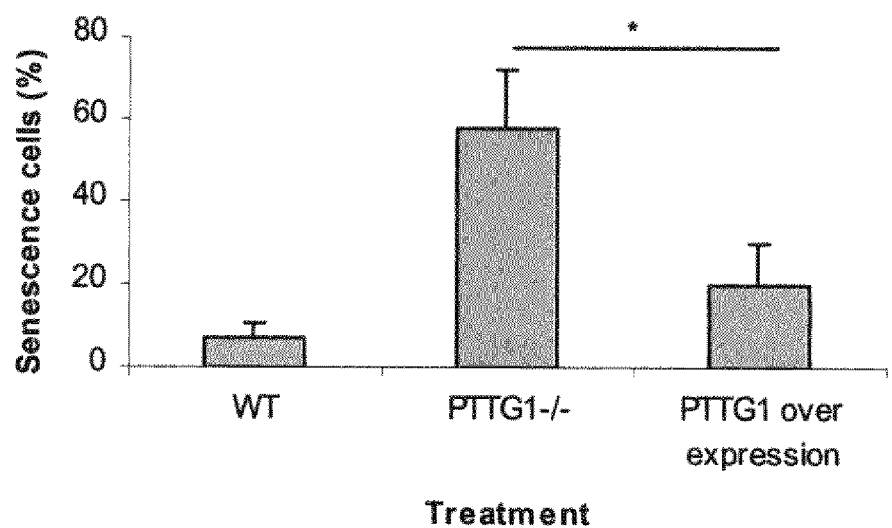

PTTG1 AS A BIOMARKER FOR CANCER TREATMENT

CROSS-REFERENCE TO RELATED APPLICATIONS

This application is the National Phase of International Application PCT/US09/37178, filed Mar. 13, 2009, which designated the U.S. and that International Application was published under PCT Article 21(2) in English. This application also claims the benefit of priority under 35 U.S.C. §119 (e) of provisional application Ser. No. 61/147,435, filed Jan. 26, 2009, and provisional application Ser. No. 61/036,524, filed Mar. 14, 2008, the contents of which are hereby incorporated by reference.

GOVERNMENT RIGHTS

This invention was made with government support provided under Grant Nos. CA 75979 and T32 DK007770 awarded by the National Institutes of Health. The U.S. government has certain rights in this invention.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Pituitary tumor transforming gene ("PTTG1"), isolated from rat pituitary tumor cells (Pei and Melmed, 1997), was subsequently identified as a securin protein (Zou et al., 1999). PTTG1 is involved in several cellular processes (Vlotides et al., 2007), including human fetal brain development (Boelaert et al., 2003), telencephalic neurogenesis (Tarabykin et al., 2000) and rat liver regeneration (Akino et al., 2005). PTTG1-null mice exhibit testicular, splenic, pancreatic beta cell and pituitary hypoplasia (Wang et al., 2001b; Wang et al., 2003; Chesnokova et al., 2005). Disrupted PTTG1 results in male-selective insulinopenic diabetes in adult mice (Wang et al., 2003). PTTG1 is abundantly expressed in most cancers and enhanced PTTG1 correlates with tumor development and size (Saez et al., 1999; McCabe et al., 2003). PTTG1 is induced early in the pathogenesis of estrogen-induced rat prolactinomas (Heaney et al., 1999) and has been suggested as a prognostic marker for differentiated thyroid and breast cancer (Solbach et al., 2004), and colon cancer invasiveness and vascularity (Heaney et al., 2000). PTTG and HTLV-1 Tax exhibit co-operative transforming activity (Sheleg et al., 2007), while small interfering RNA ("siRNA") directed against PTTG suppressed lung cancer growth in nude mice (Kakar and Malik, 2006) and was also suggested as a subcellular therapy for ovarian cancer (El-Naggar et al., 2007).

PTTG1 binds separase, inhibits cohesin cleavage and facilitates sister chromatid separation. Over-expressed PTTG1 resulted in chromosome instability and aneuploidy, which has been suggested as a mechanism underlying PTTG1 transforming activity (Wang and Melmed, 2000). PTTG1 inhibits p53 transcriptional activity (Bernal et al., 2002), and p53 stabilization is also uncoupled by loss of PTTG1 (Bernal and Hernandez, 2007). PTTG interacts with Ku, the regulatory subunit of DNA dependent protein kinase (Wang and Melmed, 2000; Pei, 2000; Pei, 2001; Chien and Pei, 2000), further indicating a role for the protein in DNA damage repair. PTTG1 also induces genetic instability in colorectal cancer cells by inhibiting double-stranded DNA repair activity (Kim et al., 2007), activates c-Myc (Pei, 2001) and bFGF (Chien and Pei, 2000), and promotes tumor angiogenesis (Zou et al., 1999; Kim et al., 2006). Dysregulated PTTG1 likely prevents mitotic exit as Cdc20 and PTTG1 double mutant embryos were unable to maintain metaphase arrest (Li et al., 2007). Although non-homologous end joining is intact in securin-deficient cells, the process occurs through aberrant end processing (Bernal et al., 2008). Using a ChIP-on-Chip assay, PTTG1 was shown to bind to multiple gene promoters (Tong et al., 2007), and PTTG1 binds to Sp1 and promotes the G1/S transition (Tong et al., 2007). This action may also contribute to PTTG1 induced cell transformation.

To further investigate PTTG1 functions, the inventors screened for PTTG1 interactions using a protein array comprising 5,000 proteins. They identified PTTG1 interacts with multiple proteins and showed that PTTG1 suppresses Aurora kinase A activity, Histone Deacetylase Inhibitor Responsiveness, as well as ROS-generating drug responsiveness in cancer treatment.

SUMMARY OF THE INVENTION

Various embodiments described herein include a method of determining the sensitivity of a cancer cell to a chemotherapeutic agent, comprising identifying the presence or absence of an upregulation of pituitary tumor transforming gene (PTTG1) in the cancer cell relative to a normal non-cancerous cell, and determining that the cancer cell lacks sensitivity to the chemotherapeutic agent if upregulation of PTTG1 is present. In another embodiment, identifying the presence of an upregulation of PTTG1 comprises detecting a level of PTTG1 activity that is at least approximately twice the level found in a normal cell. In another embodiment, the cancer cell is a HCT116 cell. In another embodiment, the chemotherapeutic agent comprises an Aurora kinase inhibitor, a histone deacetylase (HDAC) inhibitor and/or a reactive oxygen species (ROS) generating agent. In another embodiment, the Aurora kinase inhibitor is Aurora Kinase Inhibitor II or Aurora Kinase Inhibitor III. In another embodiment, the HDAC inhibitor is trichostatin A (TSA) or suberoylanilide hydroxamic acid (SAHA). In another embodiment, the ROS-generating agent is $H_2O_2$ or phenethyl isothiocyanate (PEITC).

Other embodiments include a method of diagnosing a cancer characterized by high levels of PTTG1 polypeptide relative to a normal non-cancerous subject, comprising detecting the presence or absence of a co-localization of an Aurora kinase A and a PTTG1 polypeptide in an individual, and diagnosing the cancer in the individual based upon the presence of the co-localization of the Aurora kinase A and the PTTG1 polypeptide. In another embodiment, the individual has recently received antineoplastic drug treatment. In another embodiment, the co-localization of Aurora kinase A and PTTG1 polypeptide has resulted in a compromise in the prevention of Aurora kinase A T2888 auto-phosphorylation, an inhibition of phosphorylation of Aurora kinase A substrate histone H3, and/or an abnormally condensed chromatin. In other embodiments, the co-localization of Aurora kinase A and PTTG1 polypeptide occurs near the cellular spindle and/or centrosome. In another embodiment, the PTTG1 polypeptide comprises SEQ. ID. NO.: 1. In another embodiment, the cancer comprises thyroid cancer, breast cancer, lung cancer, ovarian cancer, brain cancer, pituitary cancer and/or colon cancer. In another embodiment, the cancer is colon cancer.

Various other embodiments include a method of treating a form of cancer characterized by a high level of PTTG1 relative to a normal non-cancerous subject, comprising administering a therapeutically effective amount of a PTTG1 inhibitor, and administering a composition comprising a senescence inducing agent. In another embodiment, the senescence inducing agent is an Aurora kinase inhibitor, a HDAC inhibitor and/or a ROS-generating agent. In another embodiment, the cancer comprises thyroid cancer, breast cancer, lung cancer, brain cancer, ovarian cancer, pituitary cancer and/or colon cancer. In another embodiment, the PTTG1 inhibitor is PTTG1 siRNA.

Other features and advantages of the invention will become apparent from the following detailed description, taken in conjunction with the accompanying drawings, which illustrate, by way of example, various embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

FIG. 2 depicts the cellular location of PTTG1, in accordance with an embodiment of the present invention. PTTG1-GFP was used to identify intracellular PTTG1 location. Aurora Kinase A and separase localization was detected by antibodies as described herein. Immuno-fluorescence shows: (A) In HCT116 cells PTTG1 co-localizes with Aurora Kinase A on the spindle and centrosome in HCT116 cells as indicated by the white arrow. (B) Separase is not detected in the centrosome (white arrow) in PTTG1−/− HCT116 cells. (C) Separase is localized on the centrosome area (white arrow) in HCT116 cells. (D) PTTG1 over-expression caused abnormal chromatin structure (white arrow). Scale bar=5 μm.

FIG. 3 depicts that PTTG1 attenuates Aurora Kinase A function, in accordance with an embodiment of the present invention. (A) Over-expressed PTTG1 caused abnormal spindle formation as evidenced by unevenly distributed PTTG1-GFP and Aurora Kinase A (white arrows). (B) Western blot showing that over-expressed PTTG1 suppressed Aurora Kinase A T288 auto-phosphorylation and histone H3 Ser10 phosphorylation in HCT116 cells compared to controls. (C) Over-expressed PTTG1 repressed histone H3 Ser10 phosphorylation as shown by immunofluorescence (white arrows). Scale bar=5 μm. (D) Degradation of mitotic proteins. HCT116 cells were synchronized with 400 ng/ml nocodazole for twelve hours and mitotic cells collected by shake-off, washed and cultured in fresh medium at 37° C. to allow progression of G2/M, and cells harvested at the indicated time points. Western blot showed that PTTG1 degraded 4.5 hour and Aurora Kinase A 5.5 hour after cells were released from G2/M block. (E) In vitro kinase assay. Aurora Kinase A, histone H3 and increasing PTTG1 or GST-His levels (0.5, 1, 2 μg) were brought to a 30 μl volume reaction system as described herein. After incubations at 37° C. for 20 minutes, reactions were halted and analyzed by Western blotting using histone H3 ser10 antibody. PTTG1 dose-dependently inhibits Aurora Kinase A phosphorylation of histone H3 substrate, while GST-His has no effect at the same concentration. C1 is a control without Aurora Kinase A; C2 is a positive control (without Aurora Kinase A inhibitor).

FIG. 5 depicts that PTTG1 regulates cell response to doxorubicin, in accordance with an embodiment of the present invention. (A) PTTG1$^{-/-}$ cell growth was more sensitive to doxorubicin (mean±S.D., n=3. $P<0.05$ vs WT). Cells were seeded into 96-well plates, cultured overnight, and treated with test drug for 48 hours. Premixed WST-1 cell proliferation reagent (10 ul) was used to measure viable cells. (B) Results of colony formation assay after Aurora Kinase inhibitor III treatment (mean±S.D., n=3. $P<0.05$ vs WT). (C) Over-expressed PTTG1 rescued PTTG1$^{-/-}$ doxorubicin sensitivity (mean±S.D., n=3. $P>0.05$ vs WT); PTTG1 knock-down enhanced WT cell sensitivity to doxorubicin (mean±S.D., n=3. $P>0.05$ vs PTTG1$^{-/-}$). (D) Low dose (3 μM) Aurora Kinase inhibitor III treatment abolished the different response of WT and PTTG1$^{-/-}$ HCT116 cells to 0.63 μM doxorubicin (mean±S.D., n=3). (E) Aurora Kinase A siRNA abolished the differences in WT and PTTG1$^{-/-}$ cell response to 0.63 uM doxorubicin (mean±S.D., n=3).

FIG. 7 depicts PTTG1$^{-/-}$ HCT116 colon cancer cell lines are more sensitive to SAHA in viva WT and PTTG1$^{-/-}$ HCT116 cells were implanted subcutaneously into nude mice. SAHA (50 mg/kg, i.p. injection) daily treatment began at day 7 and continued for 17 days. Tumor volume was measured twice a week. Mice were sacrificed at day 18 and tumors were collected and weighted. The results demonstrated that PTTG1$^{-/-}$ HCT116 cells develop smaller tumors than WT cells. SAHA treatment significantly inhibited PTTG1$^{-/-}$ tumor growth (672±334 mm$^3$ vs 1434±831 mm$^3$ in control group measured at day 17, P=0.008). The WT HCT116 did not show any difference between control and treated group.

FIG. 8 depicts WT and PTTG1$^{-/-}$ HCT116 cells are implanted subcutaneously into nude mice and treated with control or SAHA for 17 days. SAHA (50 mg/kg) significantly inhibited PTTG1$^{-/-}$ tumors growth (p<0.05) but had no effect on WT tumors.

FIG. 10 depicts P21 level is higher in PTTG1$^{-/-}$ cells than WT. P21 induces senescence. The p21 level is found to be consistently higher in PTTG1$^{-/-}$ cells than WT before and after SAHA treatment. Knock down p21 reduces the enhance senescence in PTTG1$^{-/-}$ cells, demonstrating that p21 is critical for the enhanced cell senescence in PTTG1$^{-/-}$ cells.

FIG. 11 depicts PTTG1 reintroduced suppresses p21 expression and reduces senescence in PTTG1−/− cells. PTTG1 was reintroduced into PTTG1$^{-/-}$ cells and found that PTTG1 reduced p21 level and rescued SAHA induced senescence in PTTG1$^{-/-}$ HCT116 cells, demonstrating that PTTG1 regulates p21 and modulates cell senescence.

DESCRIPTION OF THE INVENTION

Figure 1:
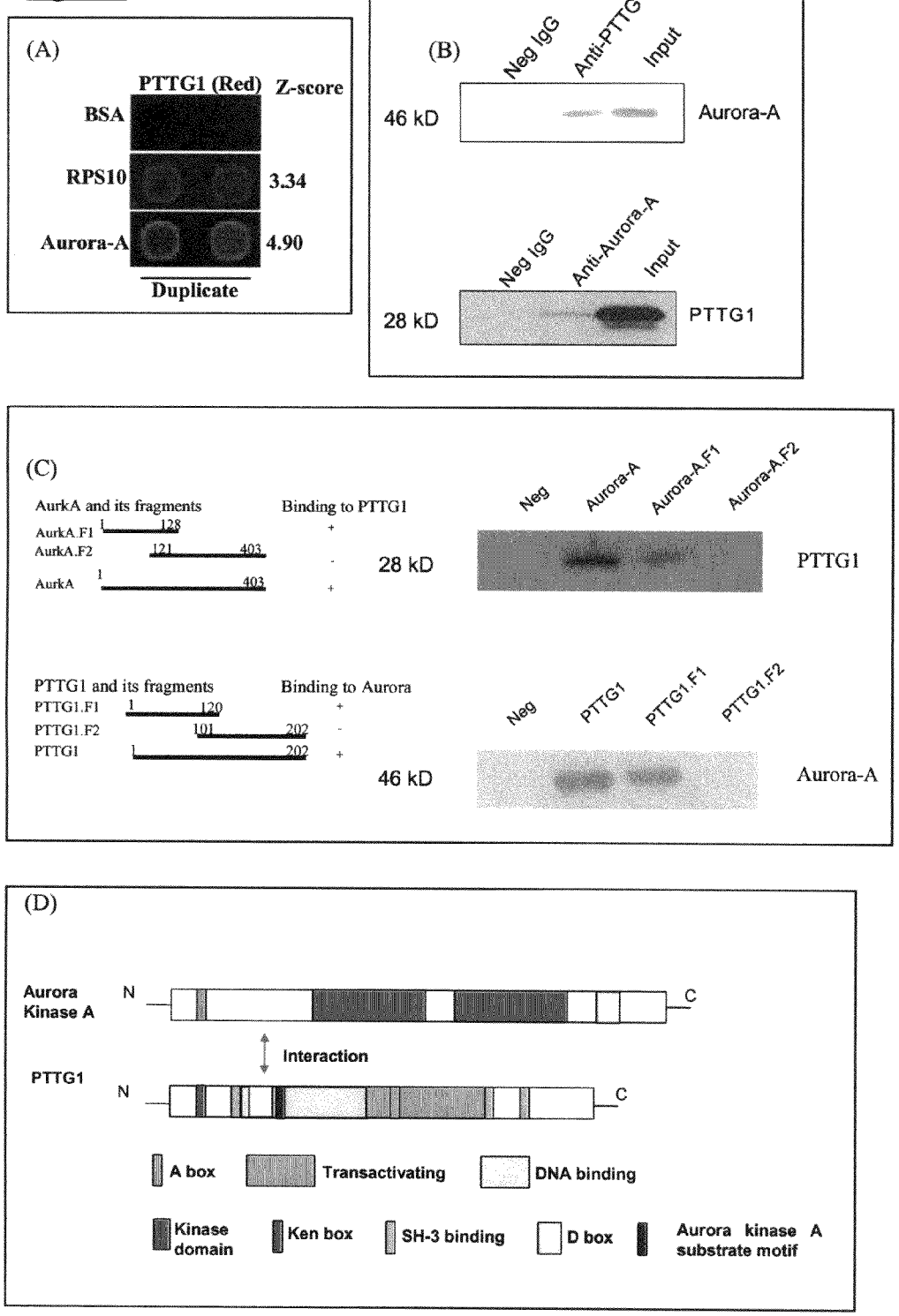
FIG. 1 depicts that PTTG1 interacts with Aurora Kinase A, in accordance with an embodiment of the present invention. (A) PTTG1 was biotin-labeled and incubated with the protein microarray. Attached biotinylated PTTG1 was probed with Streptavidin-Alexa Fluor 647 conjugate. The results show that PTTG1 binds Aurora Kinase A and ribosomal protein S10 (RPS10) but not BSA. (B) Aurora Kinase A antibody was used to co-immunoprecipitate PTTG1, and PTTG1 antibody used to co-immunoprecipitate Aurora Kinase A respectively. Western blots show that PTTG1 co-immunoprecipitated with Aurora Kinase A. (C) His Tag Aurora Kinase A, PTTG1 and their fragments were expressed using the TNT Quick Coupled Transcription/Translation system. Aurora Kinase A and its fragments were used to pull down PTTG1, or PTTG1 and its fragments were used to pull down Aurora Kinase A. The results show that PTTG1 protein binds Aurora Kinase A and its fragment 1 and Aurora Kinase A binds to PTTG1 and its fragment 1, suggesting that the two proteins interact through their respective N-termini.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"PTTG1" as used herein refers to pituitary tumor transforming gene. SEQ. ID. NO.: 1 provides an example of a PTTG1 polypeptide, and SEQ. ID. NO.: 2 provides an example of a PTTG1 polynucleotide, although the present invention is in no way limited to these examples of PTTG1.

"SAHA" as used herein refers to suberoylanilide hydroxamic acid, which may function as an HDAC inhibitor.

"HDAC" as used herein means histone deacetylase.

"ROS" as used herein means Reactive Oxygen Species, and in general, describes the varieties of oxygen-containing species that are generated along cellular metabolism. ROS, due to their highly reactive nature, possess higher reactivity than molecular oxygen that can damage DNA, proteins and lipids.

"Cancer" and "cancerous" refer to or describe the physiological condition in mammals that is typically characterized by unregulated cell growth. Examples of cancer include, but are not limited to, pituitary tumors, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer.

"Mammal" as used herein refers to any member of the class Mammalia, including, without limitation, humans and non-human primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

"Pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

"Therapeutic agent" as used herein refers to agents capable of treating tumors, other than Aurora kinase inhibitors; for example, chemotherapeutic drugs for treatment of brain tumors. Additional examples of therapeutic agents include: anti-cancer drugs, therapeutic viral particles, antiproliferative agents, antimicrobials (e.g., antibiotics, antifungals, antivirals), mood-stabilizing agents, anticonvulsants, anti-neurodegenerative agents, anti-stroke agents, cytokines, therapeutic proteins, immunotoxins, immunosuppressants, and gene therapeutics (e.g., adenoviral vectors, adeno-associated viral vectors, retroviral vectors, herpes simplex viral vectors, pox virus vectors). Other suitable therapeutic agents will be readily recognized by those of skill in the art.

"Treatment" and "treating," as used herein refer to both therapeutic treatment and prophylactic or preventative measures, wherein the object is to prevent or slow down (lessen) the targeted pathologic condition or disorder even if the treatment is ultimately unsuccessful. Those in need of treatment include those already with the disorder as well as those prone to have the disorder or those in whom the disorder is to be prevented. For example, in tumor (e.g., cancer) treatment, a therapeutic agent may directly decrease the pathology of tumor cells, or render the tumor cells more susceptible to treatment by other therapeutic agents.

"Tumor," as used herein refers to all neoplastic cell growth and proliferation, whether malignant or benign, and all precancerous and cancerous cells and tissues.

As used herein, "normal non-cancerous cell" refers to a cell that would ordinarily be found in a healthy subject that does not have or have symptoms of having cancer. Similarly, the term "normal non-cancerous subject" refers to a healthy individual who does not have or have symptoms of having cancer.

"Antineoplastic drug treatment," as used herein, refers to any of several drugs that control or kill neoplastic cells, and may be used in chemotherapy to kill cancer cells. The classification and determination of a subject as having recently received an antineoplastic drug treatment is readily ascertainable within the field. One of skill in the art may determine that an individual who previously received antineoplastic drug treatment has "recently received" the treatment, for example, 1-7 days after treatment, 3-5 weeks after treatment, 2-4 months after treatment, or up to 6 months after treatment.

PTTG1 (pituitary tumor transforming gene) is abundantly expressed in human cancers, correlates with invasiveness and clinical outcomes. As described herein, the inventors tested the role of PTTG1 in regulating anti-cancer drug responses. HCT116 colon cancer cells devoid of PTTG1 (PTTG1−/−) demonstrated enhanced sensitivity and signs of senescence in response to the HDAC (histone deacetylase) inhibitor SAHA (suberoylanilide hydroxamic acid). SAHA (0.313 uM) inhibited WT cell proliferation by 14% and PTTG1−/− cells by 49% ($p<0.001$) as measured by BrdU incorporation. b-Galactosidase staining demonstrated that 43% of PTTG1−/− cells were senescent compared to 7% of WT ($p<0.001$) when treated with 0.313 uM SAHA. SAHA did not cause apoptosis as measured by Tunel assay and activated caspase 3 levels, supporting drug-induced senescence as responsible for the observed enhanced SAHA sensitivity of PTTG1−/− cells. Treatment with SAHA enhanced p21 expression in both WT and PTTG1−/− cells. PTTG1−/− cells exhibit consistently higher levels of p21 than WT both before (2.1 fold, $p<0.05$) or after (1.8 fold, $p<0.05$) SAHA treatment. Knock down of p21 by siRNA reduced b-Galactosidase staining in PTTG1−/− cells, demonstrating p21 as important for PTTG1-mediated drug-induced senescence. Respective knock down of p53 and Sp1 both reduced p21 levels and attenuated drug-induced PTTG1−/− cell senescence. Re-introduction of PTTG1 into PTTG1−/− cells reduced p21 levels and cell sensitivity to the drug. PTTG1−/− cells exhibited higher basal histone H3 acetylation (2.3 fold, $p<0.05$), histone H4 acetylation (2.7 fold, $p<0.05$), p53 (1.8 fold, $p<0.05$), Sp1 (1.7 fold, $p<0.05$) and p300 levels (1.7 fold, $p<0.05$) than WT on the p21 promoter as assessed by ChIP (chromatin immunoprecipitation). SAHA induced both WT and PTTG1−/− histone H3 acetylation (2.8 vs 3.5 fold, $p<0.05$), histone H4 acetylation (3.4 vs 4.5 fold, $p<0.05$), p53 (1.5 vs 2.4 fold, $p<0.05$), Sp1 (3 vs 4.1 fold, $p<0.05$) and p300 (2.1 vs 2.7 fold, $p<0.05$) compared to untreated WT cells. PTTG1−/− cells have lower HDAC1 levels (0.6 fold, $p<0.05$) than WT, and HDAC1 levels at the p21 promoter region were reduced after SAHA treatment (0.4 vs 0.3, $p<0.05$) compared to untreated WT cells. In conclusion, the inventors demonstrate that PTTG1−/− HCT116 cells show enhanced p21-dependent cell senescence upon HDAC treatment. PTTG1 regulates transcription of the p21 promoter, and activates downstream p21 pathways. As cell senescence contributes to the outcome of anti-neoplastic therapy, PTTG1 can act as a biomarker to predict anti-cancer drug responses.

Similarly, as further disclosed herein, HCT116 colon cancer cells devoid of PTTG1 (PTTG1−/−) also demonstrated enhanced sensitivity to ROS-generating agents and drugs, such as $H_2O_2$ and PEITC. The BrdU incorporation assay was carried out using a commercial kit. Briefly, culture cells in 96-well microplates in a final volume of 100 ul culture medium per well. After treatment, add 10 ul BrdU labeling solution per well (final concentration: 10 uM BrdU) and incubate for 2-18 h at 37° C. Carefully remove the culture medium and wash cells twice with 250 ul wash medium containing 10% serum per well. Cells fixed and treated with nucleases working solution for 30 min at 37° C. The incorporated BrdU is detected using anti-BrdU-POD, Fab fragments and peroxidase substrate ABTS. The absorbances of the samples are measured at 405 nm against the background control, using a Victor 3 multiwell plate reader. PTTG1 knock out was confirmed using a Western Blot assay. N-acetyl cysteine (NAC), an ROS quencher was found to rescue PTTG1−/− cells sensitivity to the ROS-generating agents, demonstrating the enhanced sensitivity to ROS-generating agents is specific.

Finally, as disclosed herein, the present invention relates to the use of PTTG1 as a biomarker for Aurora kinase inhibitor responsiveness and the reduction of PTTG1 levels to enhance Aurora kinase inhibitor efficacy in cancer treatments. The invention is based, at least in part, on the inventors' discovery that a PTTG1 knock-out cancer cell line is more sensitive to Aurora kinase inhibitors relative to lines in which PTTG1 is present. Aurora kinase A is over-expressed in a variety of tumor cell lines and studies have demonstrated that the oncogenic potential of Aurora kinase A activation results in transformation of fibroblast cells and formation of multipolar mitotic spindles that induce genomic instability, which suggests their potential role in tumorigenesis. Several Aurora kinase A inhibitors have exhibited anti-cancer effects. PTTG1 appeared to inhibit Aurora kinase A; thus, the absence of PTTG1 likely enhances Aurora kinase activity, making cells more sensitive to Aurora kinase inhibitors.

In one embodiment, the invention involves the use of PTTG1 as a biomarker to predict cancer cell responsiveness to Aurora kinase inhibitors, HDAC inhibitors and/or ROS-generating agents. In another embodiment, the HDAC inhibitor includes SAHA. In another embodiment, the ROS-generating agents may include $H_2O_2$ and/or PEITC. In various embodiments, the presence of PTTG1 (or a relatively high level of PTTG1) may indicate that the cancer will be relatively less responsive to HDAC inhibitors and/or ROS-generating agents, while the absence of PTTG1 (or a relatively low level of PTTG1) may indicate that the cancer will be relatively more responsive to HDAC inhibitors and/or ROS-generating agents. Expression of PTTG1—in particular, abnormally high expression of PTTG1—can be assessed by routine techniques well known to those of skill in the art. Thus, in one embodiment, the invention relates to the determination of whether an individual will respond to Aurora kinase inhibitor therapy, HDAC inhibitor therapy and/or ROS-generating agents based on expression and/or unusually high expression of PTTG1. In another embodiment, a high level of PTTG1 expression is defined as at least approximately twice the level normally found in a healthy subject.

Another aspect of the invention involves the use of PTTG1 as a target to increase Aurora kinase inhibitors, HDAC inhibitors and/or ROS-generating agents' anti-cancer efficacy. In various embodiments of the present invention, down-regulating PTTG1 expression levels or otherwise inhibiting or silencing PTTG1 may enhance a cancer's responsiveness to Aurora kinase inhibitors, HDAC inhibitors and/or ROS-generating agents. Thus, in various embodiments, the invention includes methods for increasing the efficacy of Aurora kinase inhibitors, HDAC inhibitors and/or ROS-generating agents by down-regulating or otherwise inhibiting or silencing PTTG1 expression. In still further embodiments, the invention includes methods of treating cancer by increasing the efficacy of Aurora kinase inhibitors, HDAC inhibitors and/or ROS-generating agents therapy by down-regulating or otherwise inhibiting or silencing PTTG1 expression, and then administering a therapeutic regimen to treat the cancer wherein the regimen includes at least one Aurora kinase inhibitor, HDAC inhibitor or ROS-generating agent therapy. As will be readily appreciated by those of skill in the art, the Aurora kinase inhibitor, HDAC inhibitor and ROS-generating agent therapy can be administered alone or in combination with other therapeutic agents to deliver a clinical benefit.

In yet another embodiment, the present invention includes pharmaceutical compositions including a pharmaceutically acceptable excipient along with a therapeutically effective amount of an Aurora kinase inhibitor, HDAC inhibitor or a salt thereof or ROS-generating agent in addition to an agent that down-regulates PTTG1 expression levels or otherwise inhibits or silences PTTG1. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal or parenteral. "Parenteral" refers to a route of administration that is generally associated with injection, including intraorbital, infusion, intraarterial, intracarotid, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluents, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins PA, USA) (2000).

The present invention is also directed to a kit for treating cancer. The kit is useful for practicing the inventive method of down-regulating PTTG1 expression levels or otherwise inhibiting or silencing PTTG1, and may additionally be useful for practicing the inventive method of treating cancer with an Aurora kinase inhibitor, HDAC inhibitor or ROS-generating agent commensurate with or following the aforementioned down-regulation or inhibition/silencing of PTTG1. The kit is an assemblage of materials or components, including at least one of the inventive compositions. Thus, in some embodiments, the kit contains an agent useful in down-regulating PTTG1 expression levels or otherwise inhibiting or silencing PTTG1. In other embodiments, the kit may further include an Aurora kinase inhibitor and/or HDAC inhibitor. In other embodiments, the kit may also include an ROS-generating agent.

The exact nature of the components configured in the inventive kit depends on its intended purpose. For example, some embodiments are configured for the purpose of increasing the efficacy of Aurora kinase inhibitor, HDAC inhibitor or ROS-generating agent therapy. Other embodiments are configured for the purpose of treating cancer. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as increasing the efficacy of Aurora kinase inhibitor, HDAC inhibitor, ROS-generating agent therapy and/or treating cancer. Instructions for use may include, for example, instructions to administer a sufficient amount of an agent that down-regulates PTTG1 expression levels or otherwise inhibits or silences PTTG1, instructions to administer an Aurora kinase inhibitor, instructions to administer an HDAC inhibitor, instructions to administer an ROS-generating agent and/or a pharmaceutical composition containing either, whether alone or in addition to further therapeutic agents, and/or instructions to administer the aforementioned items via routes of administration independently selected from oral, intravenous, intraarterial, or intracarotid administration. Optionally, the kit also contains other useful components, such as syringes, catheters, applicators, pipetting or measuring tools, or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well known methods, preferably to provide a sterile, contaminant-free environment. The packaging materials employed in the kit are those customarily utilized in treating cancer. As used herein, the term "package" refers to a suitable solid matrix or material such as glass, plastic, paper, foil, and the like, capable of holding the individual kit components. The packaging material generally has an external label which indicates the contents and/or purpose of the kit and/or its components.

There are many techniques readily available in the field for detecting the presence or absence of biomarkers such as polypeptides, including protein microarrays. For example, some of the detection paradigms that can be employed to this end include optical methods, electrochemical methods (voltammetry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

Similarly, there are any number of techniques that may be employed to isolate and/or fractionate biomarkers. For example, a biomarker may be captured using biospecific capture reagents, such as antibodies, aptamers or antibodies that recognize the biomarker and modified forms of it. This method could also result in the capture of protein interactors that are bound to the proteins or that are otherwise recognized by antibodies and that, themselves, can be biomarkers. The biospecific capture reagents may also be bound to a solid phase. Then, the captured proteins can be detected by SELDI mass spectrometry or by eluting the proteins from the capture reagent and detecting the eluted proteins by traditional MALDI or by SELDI. One example of SELDI is called "affinity capture mass spectrometry," or "Surface-Enhanced Affinity Capture" or "SEAC," which involves the use of probes that have a material on the probe surface that captures analytes through a non-covalent affinity interaction (adsorption) between the material and the analyte. Some examples of mass spectrometers are time-of-flight, magnetic sector, quadrupole filter, ion trap, ion cyclotron resonance, electrostatic sector analyzer and hybrids of these.

Alternatively, for example, the presence of biomarkers maybe detected using traditional immunoassay techniques. Immunoassay requires biospecific capture reagents, such as antibodies, to capture the analytes. The assay may also be designed to specifically distinguish protein and modified forms of protein, which can be done by employing a sandwich assay in which one antibody captures more than one form and second, distinctly labeled antibodies, specifically bind, and provide distinct detection of, the various forms. Antibodies can be produced by immunizing animals with the biomolecules. Traditional immunoassays may also include sandwich immunoassays including ELISA or fluorescence-based immunoassays, as well as other enzyme immunoassays.

Prior to detection, biomarkers may also be fractionated to isolate them from other components in a solution or of blood that may interfere with detection. Fractionation may include platelet isolation from other blood components, sub-cellular fractionation of platelet components and/or fractionation of the desired biomarkers from other biomolecules found in platelets using techniques such as chromatography, affinity purification, 1D and 2D mapping, and other methodologies for purification known to those of skill in the art. In one embodiment, a sample is analyzed by means of a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Protein Microarray Screening

The human Protoarray nc3.0 study was performed as described by the manufacturer (obtained from Invitrogen Corporation; Carlsbad, Calif.). PTTG1 protein was biotinylated using biotin-XX sulfosuccinimidyl ester, purified by gel filtration, and assessed by Western blot. Appropriate protein aliquots were used to probe a protein microarray (Protoarray nc-v3; obtained from Invitrogen) and attached biotinylated PTTG1 was probed with Streptavidin-Alexa Fluor 647 conjugate. Arrays were scanned by GenePix 4000B (obtained from Molecular Devices Corporation; Sunnyvale, Calif.), and images analyzed using ProtoArray Prospector (Invitrogen).

Example 2

Poly-His Pull-Down Assays, In Vitro Transcription and Co-Immunoprecipitation TNT Quick Coupled Transcription/Translation system (obtained from Promega Corporation; Madison, Wis.) was used to generate His-PTTG1 and His-Aurora Kinase A fusion proteins. The pull-down assay was performed with ProFound Pull-Down PolyHis Protein: Protein Interaction Kit (obtained from Thermo Scientific Pierce Protein Research Products; Rockford, Ill.). Briefly, fusion proteins acting as bait were adsorbed to immobilized cobalt chelate gels. Prey proteins were biotin-lysine labeled during synthesis, and incubated with bait proteins for 1 hour at 4° C. Bound proteins were eluted and analyzed by SDS-PAGE and detected by Transcend Non-Radioactive Translation Detection Systems (Promega).

Co-immunoprecipitation was carried out with a ProFound Mammalian Co-Immunoprecipitation Kit. Control IgG and PTTG1 polyclonal antibody were conjugated to Antibody Coupling Gel and incubated overnight with HCT116 cell lysates in a rotating platform. Immunoprecipitates were eluted and analyzed by Western blotting.

Example 3

Immunofluorescence Microscopy

Cells grown on cover slips were fixed using 4% paraformaldehyde in phosphate buffer pH 7.4 for 20 min, permeabilized with 0.2% Triton X-100 in phosphate-buffered saline ("PBS") for 10 minutes, and incubated with 1% bovine serum albumin ("BSA") for 1 hour. Primary antibodies included: polyclonal Aurora Kinase A (obtained from Santa Cruz Biotechnology, Inc.; Santa Cruz, Calif.), Phospho-histone (Ser10) (obtained from Cell Signaling Technology, Inc.; Danvers, Mass.) and monoclonal separase (obtained Novus Biologicals; Littleton, Colo.) antibodies. Slides were incubated overnight at 4° C. with primary antibodies suspended in BSA 0.1% containing PBS. Cover slips were incubated with the relevant Alexa Fluor 488 or 568 secondary antibodies for two hours and with TO-PRO-3 (obtained from Invitrogen) for DNA detection for twenty minutes, then washed with PBS-BSA 0.1%, dried at room temperature (protected from light) and mounted using Prolong Gold (obtained from Invitrogen).

Images were obtained using a Leica TCS SP confocal microscope. Ar laser 488 and ArKr laser 568 was used for detection of Alexa fluorophores 488 and 568, respectively. Exclusion of auto-fluorescence was achieved by imaging with a narrow spectral detection window with the pinhole set to 1.0 Airy unit (AU) for optimal resolution. Depicted images were derived from maximum intensity projections (MIPs) of confocal stacks.

Example 4

Protein Degradation During Mitosis

Mitotic cells for degradation sequence assessment were prepared by a modified synchronization regime. Cells were released from aphidicolin (10 ng/μl) (obtained from Sigma-Aldrich Co.; St. Louis, Mo.) into medium containing 400 ng/μl nocodazole (Sigma-Aldrich) and incubated for twelve hours before harvesting by shake-off. Mitotic cells were washed three times in ice-cold PBS and replaced in 37° C. prewarmed medium. Mitotic cells were collected for analysis.

Example 5

In Vitro Kinase Activity Assay

Assays were performed using a modified Aurora kinase A assay kit obtained from Cell Signaling. Histone H3 was purchased from Promega and control His-GST protein obtained from Upstate Biotechnology, Inc. (MA). His-PTTG1 was expressed in insect cells and purified by the California Institute of Technology Protein Expression Center (Pasadena, Calif.). Aurora Kinase A and substrate histone H3 were brought to a 30 μl volume containing 25 mM Tris-HCl (pH 7.5), 10 mM $MgCl_2$, 5 mM, b-glycerophosphate, 0.1 mM $Na_3VO_4$, 20-200 μM ATP, 1 μg histone 3, 10 Units GST-Aurora Kinase A and increasing PTTG1 levels or control proteins (0.5, 1, 2 μg). Reaction mixtures were incubated at 37° C. for thirty minutes, reactions stopped by addition of 10 μl 4× Nupage LDS sample buffer, and reaction products denatured for ten minutes at 95° C. Proteins were separated by standard SDS-PAGE and analyzed by Western blotting.

Example 6

Western Blot

Protein extracts were resolved by Nupage 4-12% Bis-Tris Gel (obtained from Invitrogen). Samples were electro-blotted onto PVDF membrane (obtained from Invitrogen), and membranes blocked and incubated with primary antibody. Donkey anti-rabbit- or anti-mouse (obtained from GE Healthcare; NJ) antibodies were conjugated to horseradish peroxide to reveal immunocomplexes by enhanced chemiluminescence (obtained from Thermo Scientific Pierce Protein Research Products).

Example 7

Cell Proliferation Assay

Cell proliferation was evaluated using WST-1 cell proliferation reagent (obtained from Clontech Laboratories, Inc.; Mountain View, Calif.). Briefly, 90 μl cells were seeded into 96-well plates and cultured overnight, treated with drugs for 48 hours, and 10 μl premixed WST-1 cell proliferation reagent added. Cells were incubated for a further four hours, shaken and absorbance measured at 450 nm using a Victor 3 multiwell plate reader (obtained from PerkinElmer, Inc.; Waltham, Mass.). Cell viability rate was calculated for each well as A450 treated cells/A450 control cells×100% (A450: OD value at 450 nm).

Example 8

Anchorage-Dependent Colony Formation Assay

Briefly, 20,000 cells were plated in a six-well culture dish, allowed to attach overnight and treated with depicted drug concentrations. Cells were cultured in standard culture medium containing indicated treatments for twelve days and medium re-freshened every three days. Colonies were stained with 0.5% crystal violet in methanol/acetic acid (3:1) and those composed of >50 cells were counted.

Example 9

Site Directed Mutations

Site direct mutations were carried with QuikChange II site-directed mutagenesis kit (obtained from Stratagene, Inc.; La Jolla, Calif.) on PTTG1-PCDNA3.1. Primer sequences used for generating M9 PTTG1 mutation (S181A) are:
Sense: Described herein as SEQ. ID. NO.: 3
Antisense: Described herein as SEQ. ID. NO.: 4.

The mutant strand was synthesized using mutated primers, and digested with Dpn I to remove parental input and then used to transform competent cells. Site mutations were confirmed by sequencing.

Example 10 siRNA and Transfection

Aurora Kinase A siRNA (AM51331, Sense: Described herein as SEQ. ID. NO.: 5; Antisense: Described herein as SEQ. ID. NO.: 6) and PTTG1 siRNA (16706, Sense: Described herein as SEQ. ID. NO.: 7; Antisense: Described herein as SEQ. ID. NO.: 8) were purchased from Ambion, Inc. (TX). Transfections were carried out with lipofectamine 2000 according to protocol.

Example 11

Statistics

Analysis was performed by a standard 2-tailed Student's t test and results plotted as Mean±S.D.

Example 12

PTTG1 Interacts with Aurora Kinase A Both In Vitro and In Vivo

Protein array results showed that PTTG1 specifically interacts with several proteins. With this assay, the inventors confirmed the reported interaction of PTTG1 and ribosomal protein S10 (Pei, 1999), with a Z-score of 3.34 (FIG. 1A). PTTG1 was shown to bind specifically to Aurora Kinase A with a Z-score of 4.90, indicative of a high probability of true interaction (FIG. 1A), and the inventors used co-immunoprecipitation and a His-tag pull-down assay to confirm this interaction. As shown in FIG. 1B, using Aurora Kinase A antibody the inventors readily immunoprecipitated PTTG1 protein from whole cell extracts. Using PTTG1 antibody, Aurora Kinase A protein was also detected in the immunoprecipitated complex, indicating an in vivo interaction. In His-Tag pull-down assays, wherein expressed Aurora Kinase A, PTTG1 and their respective fragments served as bait, their respective counterparts were captured. As shown in FIG. 1C, His-tagged Aurora Kinase A and fragment 1 co-precipitated with PTTG1, while His-tagged PTTG1 and fragment 1 also pulled down Aurora Kinase A. Thus PTTG1 and Aurora Kinase A appear to interact through their respective N-termini.

Example 13

PTTG1 Co-Localizes with Aurora Kinase A on the Centrosome and Spindle

Intracellular Aurora Kinase A localization is important for mitotic control and spindle formation and intracellular Aurora Kinase A locations undergo striking changes during the cell cycle. In late G1/early S phase, Aurora Kinase A is found in pericentriolar centrosome material, and during prophase it continues its centrosomeric association at the mitotic poles, and, subsequently, at metaphase, resides in adjacent spindle microtubules (Li and Li, 2006). Due to lack of a sufficiently robust PTTG1 antibody for intracellular immunofluorescent location, the inventors monitored intracellular PTTG1 location with immunoreactive Aurora Kinase A by utilizing GFP-tagged PTTG1. As shown in FIG. 2A, PTTG1-GFP co-localized with Aurora Kinase A in the spindle and centrosome during metaphase. PTTG1 inhibits separase proteolytic activity (Hornig et al., 2002; Waizenegger et al., 2002), and, when degraded, releases separase at the metaphase to anaphase transition. As separase cleaves cohesin and promotes sister chromatid separation (Hornig et al., 2002), the inventors tested separase and Aurora Kinase A localization in HCT116 cells. As shown in FIG. 2A, separase and Aurora Kinase A co-localized mainly to the centrosome, distinct from PTTG1 and Aurora Kinase A co-localization, suggesting that the PTTG1 and Aurora Kinase A interaction occurs independently of separase. Furthermore, separase and Aurora Kinase A centrosome co-localization was not evident in cells devoid of PTTG1 (FIG. 2B), further indicating the PTTG1 requirement for centrosomic separase location. When separase levels were knocked down by RNAi, PTTG1 and Aurora Kinase A co-localization persisted (data not shown). Thus, in vivo PTTG1 binding to Aurora Kinase A appears not to involve separase, a known partner for PTTG1. The results also suggest that PTTG1 directs separase centrosomic location during mitosis, besides inhibiting separase activity. Since the duration of separase accumulation approximates the time of its activation, centrosomic separase accumulation may be important for separase activation.

Example 14

PTTG1 Inhibits Aurora Kinase A Phosphorylation of Histone H3

Aurora Kinase A is an arginine-directed kinase, which defines substrate specificity of the enzyme (Ohashi et al., 2006). As PTTG1 may serve as a substrate competitor for Aurora Kinase A activity, the inventors tested whether PTTG1 inhibits phosphorylation of the histone H3 substrate. Similar to the histone H3 Ser10 motif (Crosio et al., 2002), the PTTG1 protein sequence contains a putative Aurora Kinase A consensus motif (RXS/T) (Cheeseman et al., 2002) in the basic N-terminal domain (FIG. 1D). Aurora Kinase A modulates spindle function and chromatin condensation and also phosphorylates histone H3 (Crosio et al., 2002), a crucial event for the onset of mitosis in early G2 (Pascreau et al., 2003), as well as for mitotic chromatin condensation. The non-phosphorylated histone H3 tail participates in chromatin compaction and during mitosis, Ser10 phosphorylation weakens histone tail-DNA interactions and favors DNA-polyamine binding, thus enabling formation of highly compacted mitotic chromosomes (Prigent and Dimitrov, 2003). The inventors assayed in vitro kinase activity by incubating PTTG1, Aurora Kinase A and histone H3 in a reaction system.

As shown in FIG. 3E, when Aurora Kinase A was omitted, endogenous phosphorylated histone H3 was low, while the presence of Aurora Kinase A was associated with histone H3 phosphorylation. Addition of PTTG1 dose-dependently inhibited Aurora Kinase A histone H3 phosphorylation, suggesting a direct inhibitory effect of Aurora Kinase A activity.

The inventors then tested whether PTTG1 inhibits Aurora Kinase A activity in vivo. The phosphorylation state of histone H3 (a substrate of Aurora Kinase A) is important for chromatin condensation and de-condensation (Crosio et al., 2002) and Aurora Kinase A action depends on T288 auto-phosphorylation in the activation loop (Walter et al., 2000). The inventors therefore tested Aurora Kinase A auto-phosphorylation as well as phosphorylation of downstream histone H3 (Ser10). As shown in FIG. 3B, PTTG1-GFP over-expression in HCT116 cells resulted in decreased phosphorylation of both Aurora Kinase A and histone H3 as demonstrated by Western blot. Reduced histone H3 Ser10 phosphorylation levels also correlated with chromatin abnormalities, as shown in FIG. 3C. Next, the inventors tested whether separase inhibition induces the phenomena observed when over-expressing PTTG1. Although separase was reported to impact Aurora Kinase B (Pereira and Schiebel, 2003), reduction of separase levels caused aneuploidy but had little effect on the spindle, Aurora Kinase A distribution or chromatin condensation (data not shown), which conform to previously reported results (Waizenegger et al., 2002). These observations further suggest that PTTG1 action on Aurora Kinase A and chromatin occurs independently of separase effects.

Small molecule Aurora Kinase inhibitors have dramatic effects on chromosome morphology and spindle dynamics. Thus, the Aurora Kinase A inhibitor, ZM 447439, retards progression of chromosome condensation, leading to a disorganized spindle (Gadea and Ruderman, 2005). As shown in FIG. 3A, PTTG1 over-expression caused unequal distribution of PTTG1 and Aurora Kinase A, suggestive of spindle disorganization. Also, transfectants over-expressing PTTG1-GFP contain abnormal chromatin, likely reflecting interference with chromatin condensation and de-condensation (FIG. 3C). These results further confirm that PTTG1 inhibits Aurora Kinase A activity in vivo. As both PTTG1 and Aurora Kinase A are substrates of the APC degradation pathway, the inventors investigated the time-course of PTTG1 and Aurora Kinase A degradation during mitosis. As shown in FIG. 3D, PTTG1 is degraded about sixty minutes before Aurora Kinase A. Thus PTTG1 may inhibit Aurora Kinase A activity, and its degradation may release Aurora Kinase A for cell cycle activity.

Example 15

PTTG1-Aurora Kinase A Regulates Responses to Aurora Kinase Inhibitor III and Doxorubicin Aurora Kinase A plays a role in mitotic entry and regulating the G2 checkpoint (Marumoto et al., 2002). Abrogating DNA damage-induced G2 checkpoints may induce topoisomerase-based drug sensitivity (Vogel et al., 2005; Vogel et al., 2007). Since PTTG1 modulates Aurora Kinase A activity, the inventors tested whether PTTG1 modulates responses to anti-neoplastic drugs whose efficacy relies on a functional G2 checkpoint.

Figure 4:
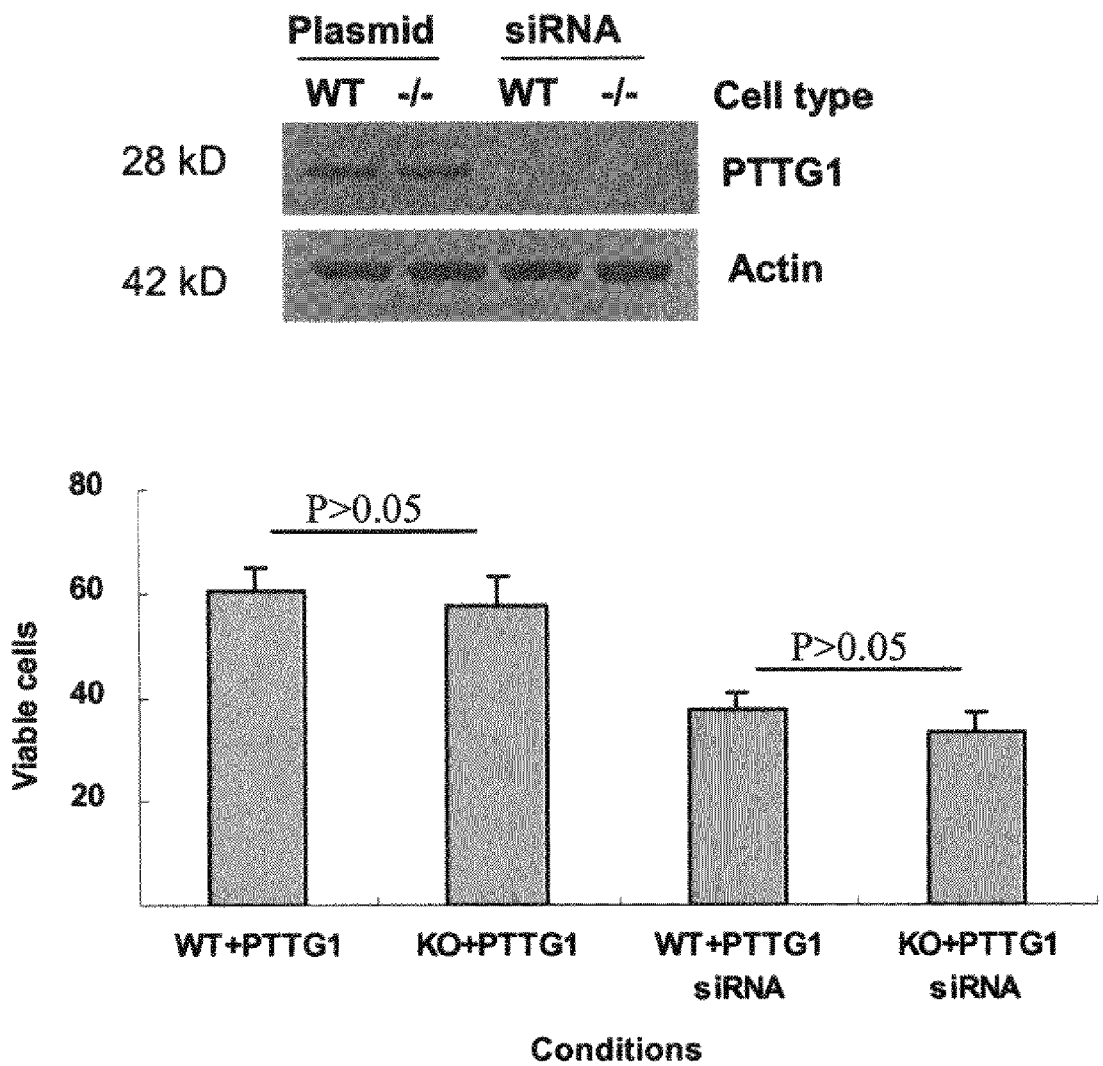
FIG. 4 depicts that PTTG1 regulates cell response to Aurora Kinase inhibition, in accordance with an embodiment of the present invention. (A) PTTG1$^{-/-}$ cell proliferation was attenuated in response to Aurora Kinase A siRNA (mean±S.D., n=3. $P<0.05$ vs WT). Cells were seeded into 96-well plates, cultured overnight, and then transfected with siRNAs (100 nM). After 72 hours, premixed WST-1 cell proliferation reagent (10 ul) was added to each well. Cells were incubated for a further four hours and shaken thoroughly for one minute before measurement. (B) PTTG1$^{-/-}$ cell growth is more sensitive to Aurora Kinase inhibitor III (mean±S.D., n=3. $P<0.05$ vs WT). Cells were seeded into 96-well plates, cultured overnight, and then treated with drug as indicated for 48 hours. Viable cells were measured using Premixed WST-1 cell proliferation reagent. (C) Anchorage-dependent colony formation assay was performed as described herein. PTTG1$^{-/-}$ cells were more sensitive to Aurora Kinase A inhibitor III than WT cells. (mean±S.D., n=3. $P<0.05$ vs WT) (D) Western blot showing that over-expressed PTTG1 rescued PTTG1$^{-/-}$ sensitivity to Aurora Kinase inhibitor III (12.5 uM) (mean±S.D., n=3. $P>0.05$ vs WT); PTTG1 knock-down enhanced WT cell sensitivity to Aurora Kinase inhibitor III (12.5 uM) (mean±S.D., n=3. $P>0.05$ vs PTTG1$^{-/-}$). PTTG1$^{-/-}$=PTTG1-null or KO cells.

Aurora Kinase A is over-expressed in a variety of tumor cell lines and acts to transform fibroblasts and form multipolar mitotic spindles inducing genomic instability (Zhou et al., 1998). As several Aurora Kinase A inhibitors exhibit anti-neoplastic effects (Mountzios et al., 2007), the inventors tested effects of Aurora Kinase A siRNA knock down in HCT116 WT and PTTG1$^{-/-}$ cells. As shown by Western blot (FIG. 4A), RNA interference efficiently knocked down Aurora Kinase A expression in both WT and PTTG1$^{-/-}$ cells, but PTTG1$^{-/-}$ cells were more sensitive to Aurora Kinase A knock down, with 62% remaining viable compared to 88% of WT cells ($p<0.05$) (FIG. 4A).

WT and PTTG1$^{-/-}$ cells were treated with Aurora Kinase Inhibitor III (Cyclopropanecarboxylic acid-(3-(4-(3-trifluoromethyl-phenylamino)-pyrimidin-2-ylamino)-phenyl)-amide; obtained from Sigma-Aldrich). As depicted in FIG. 4B, PTTG1-null HCT116 cells were more sensitive to Aurora Kinase inhibitor III, with 56% remaining viable as compared to 73% of WT cells treated with 12.5 uM for 48 h ($p<0.05$). Results of colony formation by WT and PTTG1$^{-/-}$ cells further confirmed sensitivity to Aurora Kinase inhibitor III (FIG. 4C). The inventors then re-introduced PTTG1 into PTTG1$^{-/-}$ HCT116 cells or transfected PTTG1 siRNA into WT cells to investigate the PTTG1 role in the drug response. As shown in FIG. 4D, knock down of PTTG1 increased HCT116 cell sensitivity to Aurora Kinase inhibitor III and over-expressed PTTG1 rescued the sensitivity of PTTG1$^{-/-}$ cells. The inventors also tested other, less specific Aurora Kinase inhibitors, including Aurora Kinase Inhibitor II (4-(4'-Benzamidoanilino)-6,7-dimethoxyquinazoline; obtained from Sigma-Aldrich) and Aurora Kinase/CDK inhibitor 4-(5-Amino-1-(2,6-difluorobenzoyl)-1H-[1,2,4]triazol-3-ylamino)-benzenesulfonamide on cell proliferation. HCT116 PTTG1$^{-/-}$ cells are more susceptible than WT cells to these drugs (data not shown).

PTTG1$^{-/-}$ cells are sensitive to stress and enter G2/M phase prematurely (Bernal et al., 2008). Moreover, G2 DNA damage checkpoint abrogation renders cells more sensitive to DNA damage-inducing drugs (Vogel et al., 2005; Vogel et al., 2007). While not wishing to be bound by any particular theory, the results presented herein suggest that, in the absence of PTTG1, Aurora Kinase A may be over-active upon stress, likely disrupting the G2 checkpoint, with subsequently enhanced sensitivity to DNA damage-inducing drugs. To test whether PTTG1$^{-/-}$ cell sensitivity to DNA damage is due to an attenuated G2 checkpoint unrelated to a PTTG1-Aurora Kinase A interaction, the inventors used the DNA damage agent doxorubicin to treat WT and PTTG1$^{-/-}$ HCT116 cells. As shown in FIG. 5A, PTTG1$^{-/-}$ cell proliferation was more sensitive to doxorubicin. 27% of PTTG1-/- cells remained viable as compared to 55% of WT HCT116 cells treated with 1.25 µM doxorubicin. This result was confirmed by colony formation assays, showing that after treatment of 0.16 µM doxorubicin, 36% of PTTG1$^{-/-}$ colonies survived as compared to 74% of WT colonies (FIG. 5B). As shown in FIG. 5C, over-expressing PTTG1 in PTTG1$^{-/-}$ cells rescued cancer cell susceptibility to doxorubicin, while knock down of PTTG1 in HCT116 WT cells enhanced cell sensitivity to doxorubicin treatment. The inventors then tested the role of Aurora Kinase A in response to DNA-damaging agents by using Aurora Kinase A inhibitor or siRNA. Low dose (3 µM) Aurora Kinase inhibitor III had a similar proliferation inhibitory effect on HCT116 WT and PTTG1$^{-/-}$ cell proliferation (FIG. 4B). After pre-incubation with 3 µM Aurora Kinase inhibitor III, HCT116 WT and PTTG1$^{-/-}$ cells showed a similar response to doxorubicin (FIG. 5D). The results suggest that abrogated G2 PTTG1-Aurora Kinase A may underlie PTTG1$^{-/-}$ cell sensitivity to doxorubicin. These results were further confirmed by knocking down Aurora Kinase A expression levels (FIG. 5E).

Example 16

Figure 6:
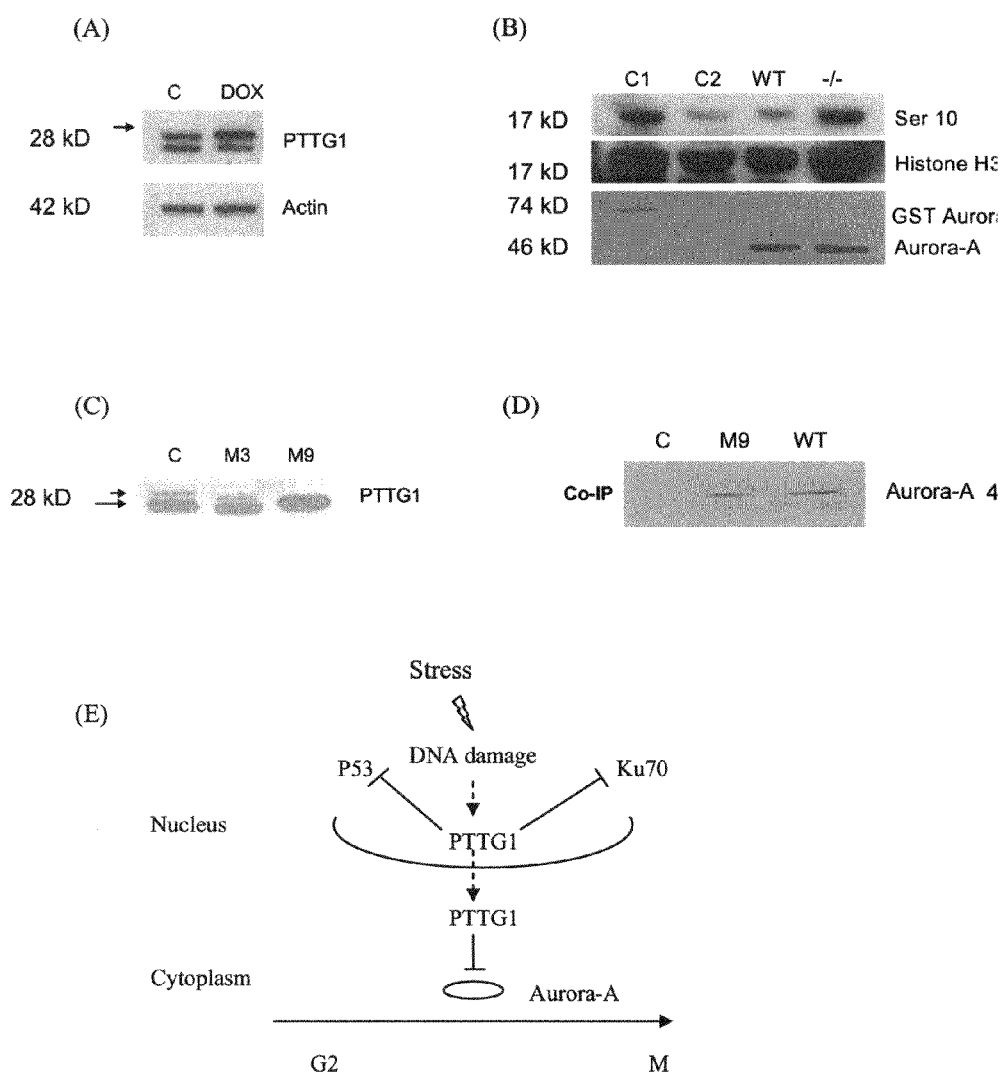
FIG. 6 depicts PTTG1 and DNA damage pathway, in accordance with an embodiment of the present invention. (A) Increased phosphorylated PTTG1 (arrowhead, shifted band) after 24 hours of 5 μM doxorubicin treatment. (B) Aurora Kinase A activity was less inhibited after DNA damage treatment in PTTG1$^{-/-}$ cells. Lane C1, positive control with Aurora Kinase A; lane C2, negative control without Aurora Kinase A; lane WT, Aurora Kinase A co-immunoprecipitated from HCT116 WT cells after doxorubicin treatment; Lane −/−, Aurora Kinase A immunoprecipitated from HCT116 PTTG1$^{-/-}$ cells after doxorubicin treatment. Aurora Kinase A activity is higher in PTTG1$^{-/-}$ than WT HCT116 cells. (C) C, PTTG1 WT plasmid; M3, PTTG1 S165A mutation; M9, PTTG1 S181A mutation. Plasmids were transfected into HCT116 PTTG1$^{-/-}$ cells and treated with proteosome inhibitor LLnL to enrich phosphorylated PTTG1. Arrow depicts the major band. The M3 mutation exhibits a lower shifted band than WT PTTG1 (arrow head), while the M9 mutation exhibits no shifted band (arrow head) suggesting impaired PTTG1 phosphorylation status. (D) WT, PTTG1 WT plasmid; M9, PTTG1 S181A mutation were transfected into HCT116 PTTG1$^{-/-}$ and co-immunoprecipitation performed. M9, a PTTG1 S181A mutation co-immunoprecipitated with Aurora Kinase A, suggesting an intact interaction. (E) Proposed signaling pathway for PTTG1 action in G2 DNA damage checkpoint.
Figure 9:
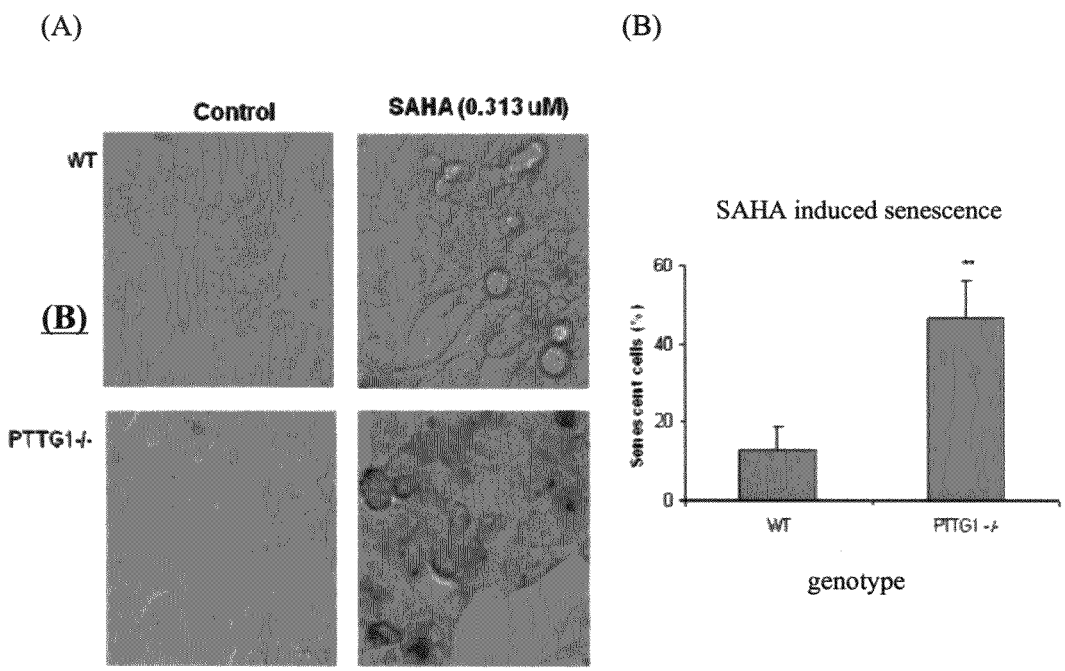
FIG. 9 depicts PTTG1−/− cells show enhanced senescence when treated with 0.313 uM SAHA. WT and HCT116 cells were treated with 0.313 uM SAHA for 48 hrs. Cells were fixed and stained with β-galactosidase staining kit (Sigma). As indicated herein, PTTG1−/− HCT116 cells demonstrated a significantly higher level of senescence (with 7% in WT and 43% in PTTG1−/−, p<0.001), supporting senescence program as responsible for the enhance cell sensitivity to antineoplastic drugs.

PTTG1-Aurora Kinase A Interaction is not Related to Phosphorylation Impairment Aurora Kinase A activity is inhibited by DNA damage (Krystyniak et al., 2006). The inventors therefore tested Aurora Kinase A activity in HCT116 WT and PTTG1$^{-/-}$ cells after treatment with doxorubicin. Immunoprecipitation and measurement of kinase activity showed that Aurora Kinase A was less suppressed in PTTG1$^{-/-}$ than WT cells treated with doxorubicin (FIG. 6B). The inventors then tested PTTG1 response to DNA damage (FIG. 6A) and showed enhanced PTTG1 phosphorylation during DNA damage drug treatments. Phosphorylated PTTG1 may therefore act with Aurora Kinase A and play a role in the DNA damage-induced G2 checkpoint. On DNA damage in yeast, pds1 (a PTTG1 analog) is phosphorylated on nine sites (Wang et al., 2001a). Human PTTG1 is phosphorylated by cdc2 at Serine 165 (Ramos-Morales et al., 2000). In screening for potential phosphorylation sites on PTTG1, the inventors found that Ser165A mutation caused less band shifting, while the Ser181A mutation abolishes most of the shifted band in Western blots (FIG. 6C), suggesting that this mutation impairs PTTG1 phosphorylation. The inventors then used this mutated PTTG1 and showed that phosphorylation-impaired PTTG1 still binds Aurora Kinase A (FIG. 6D). Thus, likely impaired phosphorylation by the PTTG1 S181A mutation is not directly involved in the PTTG1-Aurora Kinase interaction.

Example 17

PTTG1 Regulates Cancer Cell Responses to Histone Deacetylase Inhibition

PTTG1 (pituitary tumor transforming gene) is abundantly expressed in human cancers, correlates with invasiveness and clinical outcomes. As described herein, the inventors tested the role of PTTG1 in regulating anti-cancer drug responses. HCT116 colon cancer cells devoid of PTTG1 (PTTG1-/-) demonstrated enhanced sensitivity and signs of senescence in response to the HDAC (histone deacetylase) inhibitor SAHA (suberoylanilide hydroxamic acid). SAHA (0.313 uM) inhibited WT cell proliferation by 14% and PTTG1-/- cells by 49% ($p<0.001$) as measured by BrdU incorporation. b-Galactosidase staining demonstrated that 43% of PTTG1-/- cells were senescent compared to 7% of WT ($p<0.001$) when treated with 0.313 uM SAHA. SAHA did not cause apoptosis as measured by Tunel assay and activated caspase 3 levels, supporting drug-induced senescence as responsible for the observed enhanced SAHA sensitivity of PTTG1-/- cells. Treatment with SAHA enhanced p21 expression in both WT and PTTG1-/- cells. PTTG1-/- cells exhibit consistently higher levels of p21 than WT both before (2.1 fold, $p<0.05$) or after (1.8 fold, $p<0.05$) SAHA treatment. Knock down of p21 by siRNA reduced b-Galactosidase staining in PTTG1-/- cells, demonstrating p21 as important for PTTG1-mediated drug-induced senescence. Respective knock down of p53 and Sp1 both reduced p21 levels and attenuated drug-induced PTTG1-/- cell senescence. Re-introduction of PTTG1 into PTTG1-/- cells reduced p21 levels and cell sensitivity to the drug. PTTG1-/- cells exhibited higher basal histone H3 acetylation (2.3 fold, $p<0.05$), histone H4 acetylation (2.7 fold, $p<0.05$), p53 (1.8 fold, $p<0.05$), Sp1 (1.7 fold, $p<0.05$) and p300 levels (1.7 fold, $p<0.05$) than WT on the p21 promoter as assessed by ChIP (chromatin immunoprecipitation). SAHA induced both WT and PTTG1-/- histone H3 acetylation (2.8 vs 3.5 fold, $p<0.05$), histone H4 acetylation (3.4 vs 4.5 fold, $p<0.05$), p53 (1.5 vs 2.4 fold, $p<0.05$), Sp1 (3 vs 4.1 fold, $p<0.05$) and p300 (2.1 vs 2.7 fold, $p<0.05$) compared to untreated WT cells. PTTG1-/- cells have lower HDAC1 levels (0.6 fold, $p<0.05$) than WT, and HDAC1 levels at the p21 promoter region were reduced after SAHA treatment (0.4 vs 0.3, $p<0.05$) compared to untreated WT cells. In conclusion, the inventors demonstrate that PTTG1-/- HCT116 cells show enhanced p21-dependent cell senescence upon HDAC treatment. PTTG1 regulates transcription of the p21 promoter, and activates downstream p21 pathways. As cell senescence contributes to the outcome of anti-neoplastic therapy, PTTG1 may act as a biomarker to predict anti-cancer drug responses.

Example 18

BrdU Incorporation Assay and ROS-Generating Agents

The BrdU incorporation assay was carried out using a commercial kit. Briefly, culture cells in 96-well microplates in a final volume of 100 ul culture medium per well. After treatment, add 10 ul BrdU labeling solution per well (final concentration: 10 uM BrdU) and incubate for 2-18 h at 37° C. Carefully remove the culture medium and wash cells twice with 250 ul wash medium containing 10% serum per well. Cells fixed and treated with nucleases working solution for 30 min at 37° C. The incorporated BrdU is detected using anti-BrdU-POD, Fab fragments and peroxidase substrate ABTS. The absorbances of the samples are measured at 405 nm against the background control, using a Victor 3 multiwell plate reader. PTTG1 knock out was confirmed using a Western Blot assay. N-acetyl cysteine (NAC), an ROS quencher was found to rescue PTTG1-/- cells sensitivity to the ROS-generating agents, demonstrating the enhanced sensitivity to ROS-generating agents is specific.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

REFERENCES

1. Akino, K., S. Akita, T. Mizuguchi, I. Takumi, R. Yu, X. Y. Wang, J. Rozga, A. A. Demetriou, S. Melmed, A. Ohtsuru, and S. Yamashita. 2005. A Novel Molecular Marker of Pituitary Tumor Transforming Gene Involves in a Rat Liver Regeneration. *J. Surg. Res.*
2. Bernal, J. A. and A. Hernandez. 2007. p53 stabilization can be uncoupled from its role in transcriptional activation by loss of PTTG1/securin. *J. Biochem. (Tokyo)* 141:737-745.
3. Bernal, J. A., R. Luna, A. Espina, I. Lazaro, F. Ramos-Morales, F. Romero, C. Arias, A. Silva, M. Tortolero, and J. A. Pintor-Toro. 2002. Human securin interacts with p53 and modulates p53-mediated transcriptional activity and apoptosis. *Nat. Genet.* 32:306-311.
4. Bernal, J. A., M. Roche, C. Mendez-Vidal, A. Espina, M. Tortolero, and J. A. Pintor-Toro. 2008. Proliferative potential after DNA damage and non-homologous end joining are affected by loss of securin. *Cell Death. Differ.* 15:202-212.
5. Boelaert, K., L. A. Tannahill, J. N. Bulmer, S. Kachilele, S. Y. Chan, D. Kim, N. J. Gittoes, J. A. Franklyn, M. D. Kilby, and C. J. McCabe. 2003. A potential role for PTTG/securin in the developing human fetal brain. *FASEB J.* 17:1631-1639.
6. Cheeseman, I. M., S. Anderson, M. Jwa, E. M. Green, J. Kang, J. R. Yates, III, C. S. Chan, D. G. Drubin, and G. Barnes. 2002. Phospho-regulation of kinetochore-microtubule attachments by the Aurora kinase Ipl1p. *Cell* 111: 163-172.
7. Chesnokova, V., K. Kovacs, A. V. Castro, S. Zonis, and S. Melmed. 2005. Pituitary hypoplasia in Pttg-/- mice is protective for Rb+/- pituitary tumorigenesis. *Mol. Endocrinol.* 19:2371-2379.
8. Chien, W. and L. Pei. 2000. A novel binding factor facilitates nuclear translocation and transcriptional activation function of the pituitary tumor-transforming gene product. *J. Biol. Chem.* 275:19422-19427.
9. Crosio, C., G. M. Fimia, R. Loury, M. Kimura, Y. Okano, H. Zhou, S. Sen, C. D. Allis, and P. Sassone-Corsi. 2002. Mitotic phosphorylation of histone H3: spatio-temporal regulation by mammalian Aurora kinases. *Mol. Cell Biol.* 22:874-885.
10. Donangelo, I., S. Gutman, E. Horvath, K. Kovacs, K. Wawrowsky, M. Mount, and S. Melmed. 2006. Pituitary tumor transforming gene overexpression facilitates pituitary tumor development. *Endocrinology* 147:4781-4791.
11. El-Naggar, S. M., M. T. Malik, and S. S. Kakar. 2007. Small interfering RNA against PTTG: A novel therapy for ovarian cancer. *Int. J. Oncol.* 31:137-143.
12. Eyers, P. A., E. Erikson, L. G. Chen, and J. L. Maller. 2003. A novel mechanism for activation of the protein kinase Aurora A. *Curr. Biol.* 13:691-697.
13. Gadea, B. B. and J. V. Ruderman. 2005. Aurora kinase inhibitor ZM447439 blocks chromosome-induced spindle assembly, the completion of chromosome condensation, and the establishment of the spindle integrity checkpoint in Xenopus egg extracts. *Mol. Biol. Cell* 16:1305-1318.
14. Gil-Bernabe, A. M., F. Romero, M. C. Limon-Mortes, and M. Tortolero. 2006. Protein phosphatase 2A stabilizes human securin, whose phosphorylated forms are degraded via the SCF ubiquitin ligase. *Mol. Cell Biol.* 26:4017-4027.
15. Heaney, A. P., G. A. Horwitz, Z. Wang, R. Singson, and S. Melmed. 1999. Early involvement of estrogen-induced pituitary tumor transforming gene and fibroblast growth factor expression in prolactinoma pathogenesis. *Nat. Med.* 5:1317-1321.
16. Heaney, A. P., R. Singson, C. J. McCabe, V. Nelson, M. Nakashima, and S. Melmed. 2000. Expression of pituitary-tumour transforming gene in colorectal tumours. *Lancet* 355:716-719.
17. Horn, V., J. Thelu, A. Garcia, C. biges-Rizo, M. R. Block, and J. Viallet. 2007. Functional interaction of Aurora-A and PP2A during mitosis. *Mol. Biol. Cell* 18:1233-1241.
18. Hornig, N. C., P. P. Knowles, N. Q. McDonald, and F. Uhlmann. 2002. The dual mechanism of separase regulation by securin. *Curr. Biol.* 12:973-982.
19. Kakar, S. S. and M. T. Malik. 2006. Suppression of lung cancer with siRNA targeting PTTG. *Int. J. Oncol.* 29:387-395.
20. Kim, D. S., M. A. Buchanan, A. L. Stratford, J. C. Watkinson, M. C. Eggo, J. A. Franklyn, and C. J. McCabe. 2006. PTTG promotes a novel VEGF-KDR-ID3 autocrine mitogenic pathway in thyroid cancer. *Clin. Otolaryngol.* 31:246.
21. Kim, D. S., J. A. Franklyn, V. E. Smith, A. L. Stratford, H. N. Pemberton, A. Warfield, J. C. Watkinson, T. Ishmail, M. J. Wakelam, and C. J. McCabe. 2007. Securin induces genetic instability in colorectal cancer by inhibiting double-stranded DNA repair activity. *Carcinogenesis* 28:749-759.
22. Krystyniak, A., C. Garcia-Echeverria, C. Prigent, and S. Ferrari. 2006. Inhibition of Aurora A in response to DNA damage. *Oncogene* 25:338-348.
23. Li, J. J. and S. A. Li. 2006. Mitotic kinases: the key to duplication, segregation, and cytokinesis errors, chromosomal instability, and oncogenesis. *Pharmacol. Ther.* 111: 974-984.
24. Li, M., J. P. York, and P. Zhang. 2007. Loss of Cdc20 causes a securin-dependent metaphase arrest in two-cell mouse embryos. *Mol. Cell Biol.* 27:3481-3488.
25. Marumoto, T., T. Hirota, T. Morisaki, N. Kunitoku, D. Zhang, Y. Ichikawa, T. Sasayama, S. Kuninaka, T. Mimori, N. Tamaki, M. Kimura, Y. Okano, and H. Saya. 2002. Roles of aurora-A kinase in mitotic entry and G2 checkpoint in mammalian cells. *Genes Cells* 7:1173-1182.
26. McCabe, C. J., J. S. Khaira, K. Boelaert, A. P. Heaney, L. A. Tannahill, S. Hussain, R. Mitchell, J. Olliff, M. C. Sheppard, J. A. Franklyn, and N. J. Gittoes. 2003. Expression of pituitary tumour transforming gene (PTTG) and fibroblast growth factor-2 (FGF-2) in human pituitary adenomas: relationships to clinical tumour behaviour. *Clin. Endocrinol. (Oxf)* 58:141-150.
27. Mountzios, G., E. Terpos, and M. A. Dimopoulos. 2007. Aurora kinases as targets for cancer therapy. *Cancer Treat. Rev.*
28. Ohashi, S., G. Sakashita, R. Ban, M. Nagasawa, H. Matsuzaki, Y. Murata, H. Taniguchi, H. Shima, K. Furukawa, and T. Urano. 2006. Phospho-regulation of human protein kinase Aurora-A: analysis using anti-phospho-Thr288 monoclonal antibodies. *Oncogene* 25:7691-7702.

29. Pascreau, G., Y. rlot-Bonnemains, and C. Prigent. 2003. Phosphorylation of histone and histone-like proteins by aurora kinases during mitosis. *Prog. Cell Cycle Res.* 5:369-374.
30. Pei, L. 2001. Identification of c-myc as a down-stream target for pituitary tumor-transforming gene. *J. Biol. Chem.* 276:8484-8491.
31. Pei, L. 1999. Pituitary tumor-transforming gene protein associates with ribosomal protein S10 and a novel human homologue of DnaJ in testicular cells. *J. Biol. Chem.* 274: 3151-3158.
32. Pei, L. 2000. Activation of mitogen-activated protein kinase cascade regulates pituitary tumor-transforming gene transactivation function. *J. Biol. Chem.* 275:31191-31198.
33. Pei, L. and S. Melmed. 1997. Isolation and characterization of a pituitary tumor-transforming gene (PTTG). *Mol. Endocrinol.* 11:433-441.
34. Pereira, G. and E. Schiebel. 2003. Separase regulates INCENP-Aurora B anaphase spindle function through Cdc14. *Science* 302:2120-2124.
35. Prigent, C. and S. Dimitrov. 2003. Phosphorylation of serine 10 in histone H3, what for? *J. Cell Sci.* 116:3677-3685.
36. Ramos-Morales, F., A. Dominguez, F. Romero, R. Luna, M. C. Multon, J. A. Pintor-Toro, and M. Tortolero. 2000. Cell cycle regulated expression and phosphorylation of hpttg proto-oncogene product. *Oncogene* 19:403-409.
37. Saez, C., M. A. Japon, F. Ramos-Morales, F. Romero, D. I. Segura, M. Tortolero, and J. A. Pintor-Toro. 1999. hpttg is over-expressed in pituitary adenomas and other primary epithelial neoplasias. *Oncogene* 18:5473-5476.
38. Sheleg, S. V., J. M. Peloponese, Y. H. Chi, Y. Li, M. Eckhaus, and K. T. Jeang. 2007. Evidence for co-operative transforming activity of human pituitary tumor transforming gene (PTTG) and HTLV-1 Tax. *J. Virol.*
39. Solbach, C., M. Roller, C. Fellbaum, M. Nicoletti, and M. Kaufmann. 2004. PTTG mRNA expression in primary breast cancer: a prognostic marker for lymph node invasion and tumor recurrence. *Breast* 13:80-81.
40. Tarabykin, V., O. Britanova, A. Fradkov, A. Voss, L. S. Katz, S. Lukyanov, and P. Gruss. 2000. Expression of PTTG and prc1 genes during telencephalic neurogenesis. *Mech. Dev.* 92:301-304.
41. Tong, Y., Y. Tan, C. Zhou, and S. Melmed. 2007. Pituitary tumor transforming gene interacts with Sp1 to modulate G1/S cell phase transition. *Oncogene.*
42. Vlotides, G., T. Eigler, and S. Melmed. 2007. Pituitary tumor-transforming gene: physiology and implications for tumorigenesis. *Endocr. Rev.* 28:165-186.
43. Vogel, C., C. Hager, and H. Bastians. 2007. Mechanisms of mitotic cell death induced by chemotherapy-mediated G2 checkpoint abrogation. *Cancer Res.* 67:339-345.
44. Vogel, C., A. Kienitz, R. Muller, and H. Bastians. 2005. The mitotic spindle checkpoint is a critical determinant for topoisomerase-based chemotherapy. *J. Biol. Chem.* 280: 4025-4028.
45. Waizenegger, I., J. F. Gimenez-Abian, D. Wernic, and J. M. Peters. 2002. Regulation of human separase by securin binding and autocleavage. *Curr. Biol.* 12:1368-1378.
46. Walter, A. O., W. Seghezzi, W. Korver, J. Sheung, and E. Lees. 2000. The mitotic serine/threonine kinase Aurora2/AIK is regulated by phosphorylation and degradation. *Oncogene* 19:4906-4916.
47. Wang, H., D. Liu, Y. Wang, J. Qin, and S. J. Elledge. 2001a. Pds1 phosphorylation in response to DNA damage is essential for its DNA damage checkpoint function. *Genes Dev.* 15:1361-1372.
48. Wang, Z. and S. Melmed. 2000. Pituitary tumor transforming gene (PTTG) transforming and transactivation activity. *J. Biol. Chem.* 275:7459-7461.
49. Wang, Z., E. Moro, K. Kovacs, R. Yu, and S. Melmed. 2003. Pituitary tumor transforming gene-null male mice exhibit impaired pancreatic beta cell proliferation and diabetes. *Proc. Natl. Acad. Sci. U.S.A* 100:3428-3432.
50. Wang, Z., R. Yu, and S. Melmed. 2001b. Mice lacking pituitary tumor transforming gene show testicular and splenic hypoplasia, thymic hyperplasia, thrombocytopenia, aberrant cell cycle progression, and premature centromere division. *Mol. Endocrinol.* 15:1870-1879.
51. Zhou, H., J. Kuang, L. Zhong, W. L. Kuo, J. W. Gray, A. Sahin, B. R. Brinkley, and S. Sen. 1998. Tumour amplified kinase STK15/BTAK induces centrosome amplification, aneuploidy and transformation. *Nat. Genet.* 20:189-193.
52. Zou, H., T. J. McGarry, T. Bernal, and M. W. Kirschner. 1999. Identification of a vertebrate sister-chromatid separation inhibitor involved in transformation and tumorigenesis. *Science* 285:418-422.

The invention claimed is:

1. A method of predicting the sensitivity of a cancer cell to a chemotherapeutic agent, comprising:

identifying the presence or absence of an upregulation of pituitary tumor transforming gene (PTTG1) in the cancer cell relative to a normal non-cancerous cell, and predicting that the cancer cell lacks sensitivity to the chemotherapeutic agent if upregulation of PTTG1 is present.

2. The method of claim 1, wherein identifying the presence of an upregulation of PTTG1 comprises detecting a level of PTTG1 activity that is at least approximately twice the level found in a normal non-cancerous cell.

3. The method of claim 1, wherein the cancer cell is a HCT116 cell.

4. The method of claim 1, wherein the chemotherapeutic agent comprises an Aurora kinase inhibitor, a histone deacetylase (HDAC) inhibitor and/or a reactive oxygen species (ROS) generating agent.

5. The method of claim 4, wherein the Aurora kinase inhibitor is Aurora Kinase Inhibitor II or Aurora Kinase Inhibitor III.

6. The method of claim 4, wherein the HDAC inhibitor is trichostatin A (TSA) or suberoylanilide hydroxamic acid (SAHA).

7. The method of claim 4, wherein the ROS-generating agent is $H_2O_2$ or phenethyl isothiocyanate (PEITC).

* * * * *

SEQUENCE LISTING

```
<160> NUMBER OF SEQ ID NOS: 8

<210> SEQ ID NO 1
<211> LENGTH: 202
<212> TYPE: PRT
<213> ORGANISM: Homo sapiens

<400> SEQUENCE: 1

Met Ala Thr Leu Ile Tyr Val Asp Lys Glu Asn Gly Glu Pro Gly Thr
1               5                   10                  15

Arg Val Val Ala Lys Asp Gly Leu Lys Leu Gly Ser Gly Pro Ser Ile
            20                  25                  30

Lys Ala Leu Asp Gly Arg Ser Gln Val Ser Thr Pro Arg Phe Gly Lys
        35                  40                  45

Thr Phe Asp Ala Pro Pro Ala Leu Pro Lys Ala Thr Arg Lys Ala Leu
    50                  55                  60
```

```
Gly Thr Val Asn Arg Ala Thr Glu Lys Ser Val Lys Thr Lys Gly Pro
 65                  70                  75                  80

Leu Lys Gln Lys Gln Pro Ser Phe Ser Ala Lys Lys Met Thr Glu Lys
                 85                  90                  95

Thr Val Lys Ala Lys Ser Ser Val Pro Ala Ser Asp Asp Ala Tyr Pro
            100                 105                 110

Glu Ile Glu Lys Phe Phe Pro Phe Asn Pro Leu Asp Phe Glu Ser Phe
        115                 120                 125

Asp Leu Pro Glu Glu His Gln Ile Ala His Leu Pro Leu Ser Gly Val
    130                 135                 140

Pro Leu Met Ile Leu Asp Glu Glu Arg Glu Leu Glu Lys Leu Phe Gln
145                 150                 155                 160

Leu Gly Pro Pro Ser Pro Val Lys Met Pro Ser Pro Pro Trp Glu Ser
                165                 170                 175

Asn Leu Leu Gln Ser Pro Ser Ser Ile Leu Ser Thr Leu Asp Val Glu
            180                 185                 190

Leu Pro Pro Val Cys Cys Asp Ile Asp Ile
        195                 200

<210> SEQ ID NO 2
<211> LENGTH: 728
<212> TYPE: DNA
<213> ORGANISM: Homo sapiens

<400> SEQUENCE: 2
gcggcctcag atgaatgcgg ctgttaagac ctgcaataat ccagaatggc tactctgatc      60
tatgttgata aggaaaatgg agaaccaggc acccgtgtgg ttgctaagga tgggctgaag     120
ctggggtctg gaccttcaat caaagcctta gatgggagat ctcaagtttc aacaccacgt     180
tttggcaaaa cgttcgatgc cccaccagcc ttacctaaag ctactagaaa ggctttggga     240
actgtcaaca gagctacaga aaagtctgta aagaccaagg gaccccctcaa acaaaaacag    300 ccaagctttt ctgccaaaaa gatgactgag aagactgtta agcaaaaag ctctgttcct      360 gcctcagatg atgcctatcc agaaatagaa aaattctttc ccttcaatcc tctagacttt    420
gagagttttg acctgcctga gagcaccag attgcgcacc tccccttgag tggagtgcct     480
ctcatgatcc ttgacgagga gagagagctt gaaaagctgt ttcagctggg ccccccttca    540
cctgtgaaga tgccctctcc accatgggaa tccaatctgt tgcagtctcc ttcaagcatt    600
ctgtcgaccc tggatgttga attgccacct gtttgctgtg acatagatat ttaaatttct    660
tagtgcttca gagtttgtgt gtatttgtat taataaagca ttcttcaaca gaaaaaaaaa    720
aaaaaaaa                                                             728

<210> SEQ ID NO 3
<211> LENGTH: 32
<212> TYPE: DNA
<213> ORGANISM: Homo sapiens

<400> SEQUENCE: 3
gggaatccaa tctgttgcag tctccttcaa gc                                    32

<210> SEQ ID NO 4
<211> LENGTH: 32
<212> TYPE: DNA
<213> ORGANISM: Homo sapiens

<400> SEQUENCE: 4
gggaatccaa tctgttgcag gctccttcaa gc                                    32
```

```
<210> SEQ ID NO 5
<211> LENGTH: 19
<212> TYPE: RNA
<213> ORGANISM: Homo sapiens

<400> SEQUENCE: 5
ggcaaccagu guaccucau                                              19

<210> SEQ ID NO 6
<211> LENGTH: 19
<212> TYPE: RNA
<213> ORGANISM: Homo sapiens

<400> SEQUENCE: 6
augagguaca cugguugcc                                              19

<210> SEQ ID NO 7
<211> LENGTH: 19
<212> TYPE: RNA
<213> ORGANISM: Homo sapiens

<400> SEQUENCE: 7
gucuguaaag accaaggga                                              19

<210> SEQ ID NO 8
<211> LENGTH: 19
<212> TYPE: RNA
<213> ORGANISM: Homo sapiens

<400> SEQUENCE: 8
ucccuugguc uuuacagac                                              19
```